United States Patent
Van Egmond et al.

(10) Patent No.: US 7,214,846 B2
(45) Date of Patent: May 8, 2007

(54) RECOVERY OF ETHYLENE AND PROPYLENE FROM A METHANOL TO OLEFIN REACTION SYSTEM

(75) Inventors: Cornelis F. Van Egmond, Pasadena, TX (US); David Jon Duhon, Kingwood, TX (US); John Ernest Asplin, Singapore (SG)

(73) Assignee: ExxonMobil Chemical Patents Inc., Houston, TX (US)

( * ) Notice: Subject to any disclaimer, the term of this patent is extended or adjusted under 35 U.S.C. 154(b) by 576 days.

(21) Appl. No.: 10/635,410

(22) Filed: Aug. 6, 2003

(65) Prior Publication Data
US 2005/0033103 A1 Feb. 10, 2005

(51) Int. Cl.
*C07C 1/20* (2006.01)
(52) U.S. Cl. .................. 585/809; 585/638; 585/820; 585/639
(58) Field of Classification Search ............... 585/809, 585/638, 820, 639
See application file for complete search history.

(56) References Cited

U.S. PATENT DOCUMENTS

| | | | | |
|---|---|---|---|---|
| 4,474,647 | A | 10/1984 | Asselineau et al. | 203/49 |
| 4,587,373 | A | 5/1986 | Hsia | 585/639 |
| 4,898,717 | A | 2/1990 | Hsia et al. | 422/190 |
| 5,122,236 | A | 6/1992 | Smith, Jr. et al. | 203/43 |
| 5,336,841 | A | 8/1994 | Adams | 203/28 |
| 5,609,734 | A | 3/1997 | Streicher et al. | 203/39 |
| 5,723,686 | A | 3/1998 | Patton et al. | 568/697 |
| 5,811,621 | A | 9/1998 | van Dijk | 585/639 |
| 5,908,964 | A | 6/1999 | Koskinen et al. | 568/697 |
| 6,121,504 | A | 9/2000 | Kuechler et al. | 585/640 |
| 6,303,841 | B1 | 10/2001 | Senetar et al. | 585/809 |
| 6,444,869 | B2 | 9/2002 | Senetar et al. | 585/639 |
| 6,855,858 | B2 * | 2/2005 | Cheng et al. | 585/809 |
| 2003/0004386 | A1 | 1/2003 | Lattner et al. | |
| 2004/0039239 | A1 | 2/2004 | Shutt | |
| 2004/0122272 | A1 | 6/2004 | Van Egmond et al. | |

FOREIGN PATENT DOCUMENTS

WO 03/020673 3/2003
WO 03/020678 3/2003

OTHER PUBLICATIONS

U.S. Appl. No. 10/124,859, filed Apr. 18, 2002, Ding et al.
U.S. Appl. No. 10/125,138, filed Apr. 18, 2002, Van Egmond et al.
U.S. Appl. No. 10/292,232, filed Nov. 12, 2002, Ding et al.

* cited by examiner

*Primary Examiner*—Tam M. Nguyen

(57) ABSTRACT

The present invention provides new highly-efficient separation processes and systems for separating polymerization-grade ethylene and propylene from an initial effluent stream comprising ethane, ethylene, propylene, dimethyl ether, and one or more of propane, acetylene, methyl acetylene, propadiene, methane, hydrogen, carbon monoxide, carbon dioxide and $C_4+$ components. In one embodiment, the initial effluent stream is provided from a methanol-to-olefin reaction system. It has been discovered that an efficient separation of these components is realized when DME is partially removed in a first separation step comprising methanol and water washing steps, followed by separation of the remaining components in additional separation steps.

91 Claims, 3 Drawing Sheets

RECOVERY OF ETHYLENE AND PROPYLENE FROM A METHANOL TO OLEFIN REACTION SYSTEM

FIELD OF THE INVENTION

The present invention relates to ethylene and propylene recovery systems. More particularly, the present invention relates to recovering ethylene and propylene from a mixed effluent stream comprising one or more of methane, dimethyl ether, ethane, ethylene, propane, propylene and acetylene.

BACKGROUND OF THE INVENTION

Light olefins such as ethylene and propylene are important commodity petrochemicals useful in a variety of processes for making plastics and other chemical compounds. Ethylene is used to make various polyethylene plastics, and in making other chemicals such as vinyl chloride, ethylene oxide, ethylbenzene and alcohol. Propylene is used to make various polypropylene plastics, and in making other chemicals such as acrylonitrile and propylene oxide. The petrochemical industry has known for some time that oxygenates, especially alcohols, are convertible into light olefins. The preferred conversion process is generally referred to as an oxygenate-to-olefin (OTO) or specifically to methanol-to-olefins (MTO) process, where methanol is converted to primarily ethylene and/or propylene in the presence of a molecular sieve catalyst.

Various byproducts are produced in the MTO reaction process. These byproducts may include components that are heavier than propane and propylene, such as $C_4+$ components (olefinic and aliphatic) as well as multiply unsaturated components such as acetylene, methyl acetylene and propadiene. Oxygenate compounds such as alcohols, aldehydes, ketones, esters, acids and ethers in the C1 to C6 range as well as trace quantities of aromatic compounds may also be formed in MTO reactors or in MTO effluent processing. Additionally, a small amount of oxygenate from the feedstock, e.g., methanol and/or dimethyl ether ("DME"), can pass through the MTO reactor with the product effluent without being converted to desired product. As a result of oxygenate synthesis and/or oxygenate "pass through" in an MTO reactor system, the effluent from an MTO reactor can contain undesirably high concentrations of oxygenate compounds. These oxygenates, particularly light oxygenates, are in amounts that would make the ethylene and propylene off-specification for their preferred dispositions, e.g., polymerization.

Various processing schemes have been developed for separating one or more of these components from non-MTO effluent streams. For example, U.S. Pat. No. 5,336,841 to Adams is directed to a process for removing oxygenates from a C4 raffinate stream from an MTBE plant. A backcracking catalyst is placed into the bottom of an oxygenate removal column, which converts any MTBE or tertiary butyl alcohol contained therein back to their original components of isobutene and methanol or water. The raffinate stream is first subjected to a water wash to remove the gross amounts of methanol and DME.

U.S. Pat. No. 5,122,236 to Smith et al. is directed to a process for removing DME and methanol impurities from a C4 hydrocarbon stream without substantial loss of C4 hydrocarbons by fractionating a C4 hydrocarbon stream containing DME and methanol at low levels, e.g., less than 5 weight percent, to produce an overhead of about 20 to 40 volume percent of the C4 stream, condensing the overhead, contacting the condensed overhead with about 1 to 5 volumes of water, thereby removing a portion of the DME and methanol from the C4 stream, returning substantially all of the C4 stream, except the small amount solubilized in the water, to the fractionation and flashing the solubilized DME and hydrocarbons from the water.

U.S. patent application Ser. No. 10/292,232 filed Nov. 12, 2002, the entirety of which is incorporated herein by reference, is directed to a particularly desirable process for recovering C4 olefins from a product stream comprising C4 olefins, dimethyl ether and C5+ hydrocarbons. The process includes first separating out C5+ hydrocarbons and coboiling oxygenates, if any, from a stream comprising C5+ hydrocarbons, DME and C4 hydrocarbons. By first separating out the C5+ hydrocarbons and coboiling oxygenates, a more efficient separation of DME from C4 olefins by water wash is obtainable.

Although a variety of processes have been described for separating $C_4+$ components from C3– components, separation schemes for efficiently recovering ethylene and propylene from other C3– components in a mixed effluent stream have not been widely described and have heretofore proven generally inefficient. Specifically, recovery of ethylene and propylene from lighter less desirable components, particularly from DME, has proven inefficient when the effluent stream contains a mixture of methane, DME, ethane, ethylene, propane and propylene. Thus, a need exists for efficiently separating ethylene and propylene from an MTO reaction system effluent stream containing these C3– components, or from a similar effluent stream derived from another reaction process.

SUMMARY OF THE INVENTION

The present invention provides novel process flow schemes, which produce on-spec ethylene and propylene product streams for polymer feedstock disposition from an initial effluent stream comprising dimethyl ether (DME), ethane, ethylene, propylene, and, optionally, one or more of propane, acetylene, methyl acetylene, propadiene, methane, hydrogen, carbon monoxide, carbon dioxide and $C_4+$ components. The process flow schemes are highly efficient in removing DME and minimizing equipment count. A particularly efficient separation of these components can be realized when DME is selectively removed, at least partially, in a first separation step, followed by separation of the remaining components in additional separation steps. Preferably, at least a portion of the DME is removed in methanol and water washing steps. Moreover, the process flow schemes ensure thorough acetylene conversion by integrating one or more hydrogenation converters therein. Unless otherwise stated herein, a "majority" or a "minority" of a specified composition means a weight majority and a weight minority, respectively.

In one embodiment, the invention is a process for removing dimethyl ether from an olefin-containing effluent stream. In this embodiment, an effluent stream is provided, which comprises ethane, ethylene, propane, propylene and dimethyl ether. The effluent stream contacts an oxygenate removal medium in an oxygenate removal unit under conditions effective to form a first overhead stream and a first bottoms stream. The first overhead stream comprises residual oxygenate removal medium and a majority of the ethane, ethylene, propane, propylene, and dimethyl ether. The first bottoms stream comprises a minority of the dimethyl ether and a majority of the oxygenate removal medium. Optionally, the oxygenate-removal medium is selected from the group consisting of methanol and tri (ethylene glycol). The first overhead stream contacts water under conditions effective to form a second overhead stream and a second bottoms stream, wherein the second overhead stream comprises a majority of the ethane, ethylene, propane, propylene, and dimethyl ether present in the first overhead stream, and wherein the second bottoms stream comprises a majority of the residual oxygenate removal medium and a majority of the water. At least a portion of the second overhead stream is separated into a third overhead stream and a third bottoms stream, wherein the third overhead stream comprises a majority of the propylene and optionally a majority of the ethane, ethylene and light ends present in the at least a portion of the second overhead stream, and wherein the third bottoms stream comprises a majority of the propane and dimethyl ether present in the at least a portion of the second overhead stream.

Optionally, at least a portion of the second overhead stream, described above, is separated into a third overhead stream and a third bottoms stream, wherein the third overhead stream comprises a majority of the ethane and ethylene present in the at least a portion of the second overhead stream, and wherein the third bottoms stream comprises a majority of the propane, propylene and dimethyl ether present in the at least a portion of the second overhead stream. At least a portion of the third bottoms stream is then separated into a fourth overhead stream and a fourth bottoms stream, wherein the fourth overhead stream comprises a majority of the propylene present in the at least a portion of the third bottoms stream, and wherein the fourth bottoms stream comprises a majority of the propane and dimethyl ether present in the at least a portion of the third bottoms stream.

BRIEF DESCRIPTION OF THE DRAWINGS

This invention will be better understood by reference to the Detailed Description of the Invention when taken together with the attached drawings, wherein.

DETAILED DESCRIPTION OF THE INVENTION

Introduction

The present invention provides new highly-efficient separation processes and systems for separating polymerization-grade ethylene and propylene from an "initial effluent stream," defined herein as a stream containing dimethyl ether (DME), ethane, ethylene and propylene. Additionally, the initial effluent stream optionally includes one or more of propane, acetylene, methyl acetylene, propadiene, methane, hydrogen, carbon monoxide, carbon dioxide and $C_4$+ components (aliphatic and/or olefinic). In one particularly preferred embodiment, the initial effluent stream is derived from the product effluent of a methanol-to-olefin (MTO) reaction process, described in detail below. It has been discovered that an efficient separation of DME from the other components in the initial effluent stream can be realized when DME is selectively removed, at least partially, in a first washing step, followed by separation of the remaining components in additional separation steps.

The Initial Effluent Stream

The initial effluent stream may be derived from a variety of sources. For example, in one embodiment, the initial effluent stream is derived from a product effluent of a reaction selected from the group consisting of an olefin interconversion reaction, an oxygenate to olefin (OTO) reaction, an oxygenate to gasoline conversion reaction, malaeic anhydride formulation, vapor phase methanol synthesis, phthalic anhydride formulation, a Fischer Tropsch reaction, and an acrylonitrile formulation. Preferably, the initial effluent stream is derived from an effluent stream of an MTO reaction system.

Although the initial effluent stream can be derived from any conventional source that contains ethane, ethylene, propylene and DME, the invention is particularly suited to removing DME and other oxygenates from an initial effluent stream derived from an OTO process or, particularly, from an MTO process. Thus, in one embodiment of this invention, an initial effluent stream containing DME is derived from a product effluent stream of a reaction system, wherein an oxygenate feedstock contacts a molecular sieve catalyst under conditions effective to form light olefins, as described in more detail below.

An MTO reaction system produces a product effluent stream, which includes a minor amount of $C_4$+ components (olefin and aliphatic) in addition to ethane, ethylene, DME, propane and propylene. The product effluent also may include one or more of hydrogen, methane, carbon monoxide, carbon dioxide, acetylene, methyl acetylene and propadiene. One non-limiting system for forming the initial effluent stream from an MTO reaction system is discussed in more detail below with reference to FIG. 3.

Figure 3:
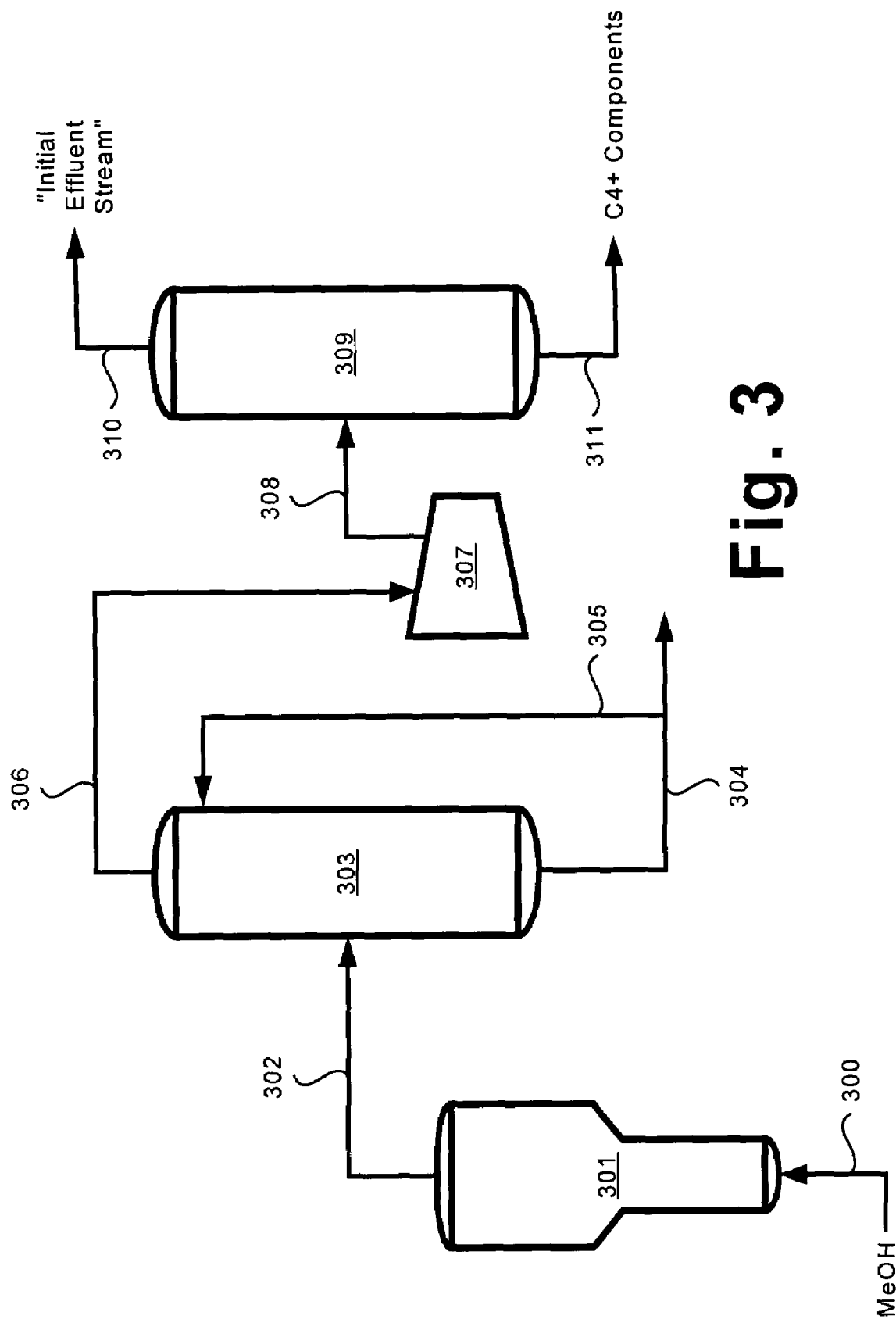
FIG. 3 illustrates an OTO reaction unit, quench unit and compression sequence.

FIG. 3 illustrates one process for deriving an initial effluent stream containing ethane, ethylene, DME and propylene, and optionally $C_4$+ components from an MTO reaction system. In FIG. 3, methanol is sent through line 300 to an MTO reactor 301 wherein the methanol is converted to light olefins, which exit the MTO reactor 301 in olefin-containing stream 302. Light olefin-containing stream 302 comprises methane, ethylene, ethane, propylene, propane, DME, water, a minor amount of $C_4$+ components, and other hydrocarbon and oxygenate components. The olefin-containing stream 302 is directed to a quench tower 303 wherein the olefin-containing stream 302 is cooled and water and other readily condensable components are condensed.

The condensed components, which comprise a substantial amount of water, are withdrawn from the quench tower 303 through a bottoms line 304. A portion of the condensed components are circulated through line 305 back to the top of the quench tower 303. The line 305 contains a cooling unit, e.g., heat exchanger, not shown, to cool the condensed components so as to provide a cooling medium to cool the components in quench tower 303.

Olefin-containing vapor is yielded from the quench tower 303 through a quench overhead stream 306. The olefin-containing vapor is compressed in one or more compressors 307 to form a compressed stream 308. As shown, the compressed stream 308 is directed to a $C_4$+ component removal unit 309, e.g., a depropanizer prior to light ends separation or C2/C3 separation. The $C_4$+ components typically contain foulants such as butadiene. As a result, the $C_4$+ components preferably are removed before removal of light ends, before C2/C3 separation, before the washing steps of the present invention, and before removal of the other components contained in the initial effluent stream. It is contemplated, however, as described in detail below, that the C$_4$+ component removal unit 309 optionally may be disposed in the downstream separation and processing system according to several alternative embodiments of the present invention. Reverting to FIG. 3, in the C$_4$+ component removal unit 309, the compressed stream 308 is subjected to conditions, e.g., temperature and pressure, sufficient to separate the compressed stream 308 into a C3− stream 310, e.g., the initial effluent stream, and a C$_4$+ stream 311. The C3− stream 310 contains a majority of the C3− components, e.g., light ends, ethane, ethylene, propane, DME and propylene, present in the compressed stream 308, while the C$_4$+ stream 311 contains a majority of the C$_4$+ components, e.g., butane, butylene, butadiene, pentanes and heavier components, present in the compressed stream 308.

Figure 1:
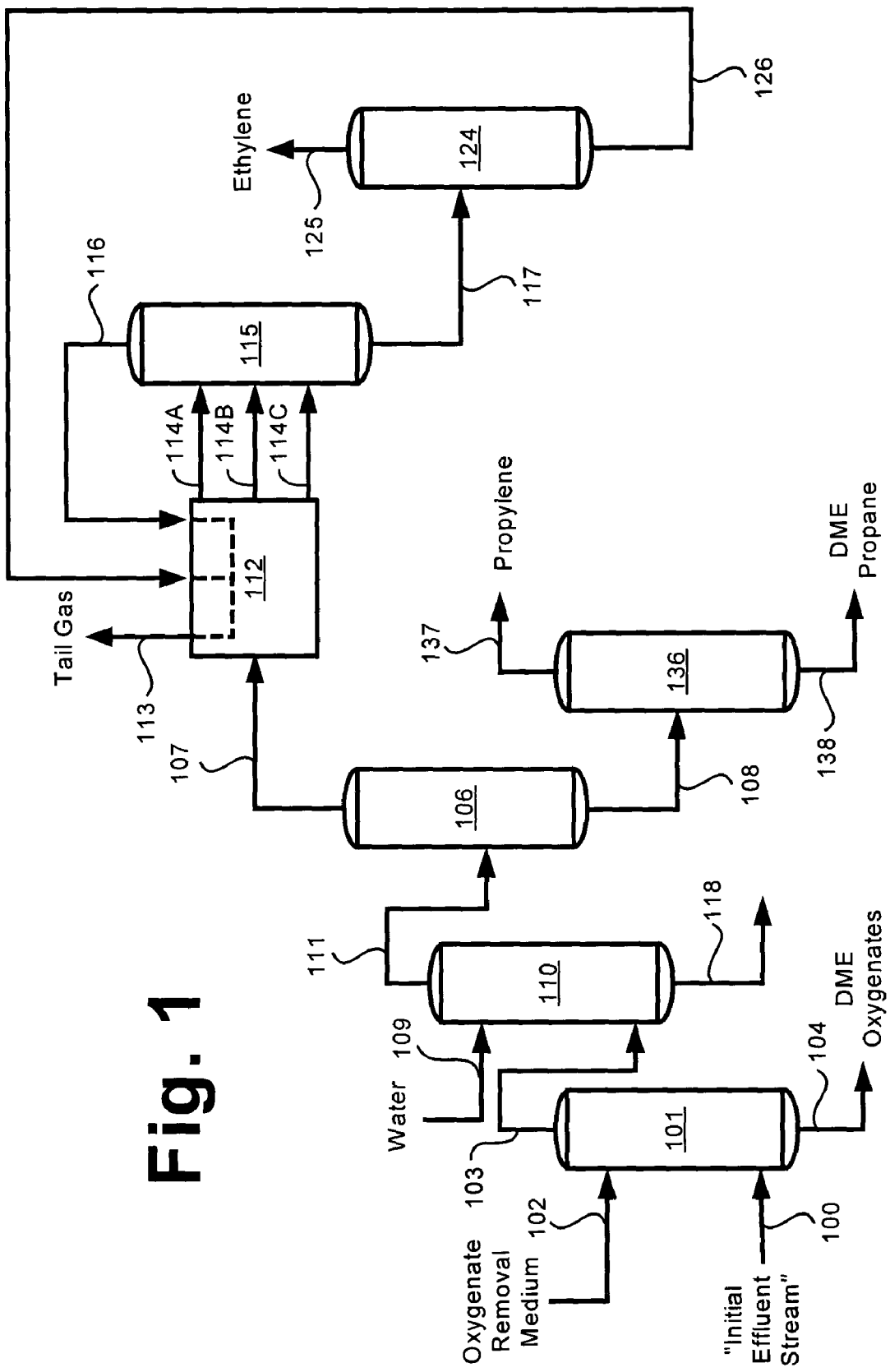
FIG. 1 illustrates a separation scheme according to one embodiment of the present invention.
Figure 2:
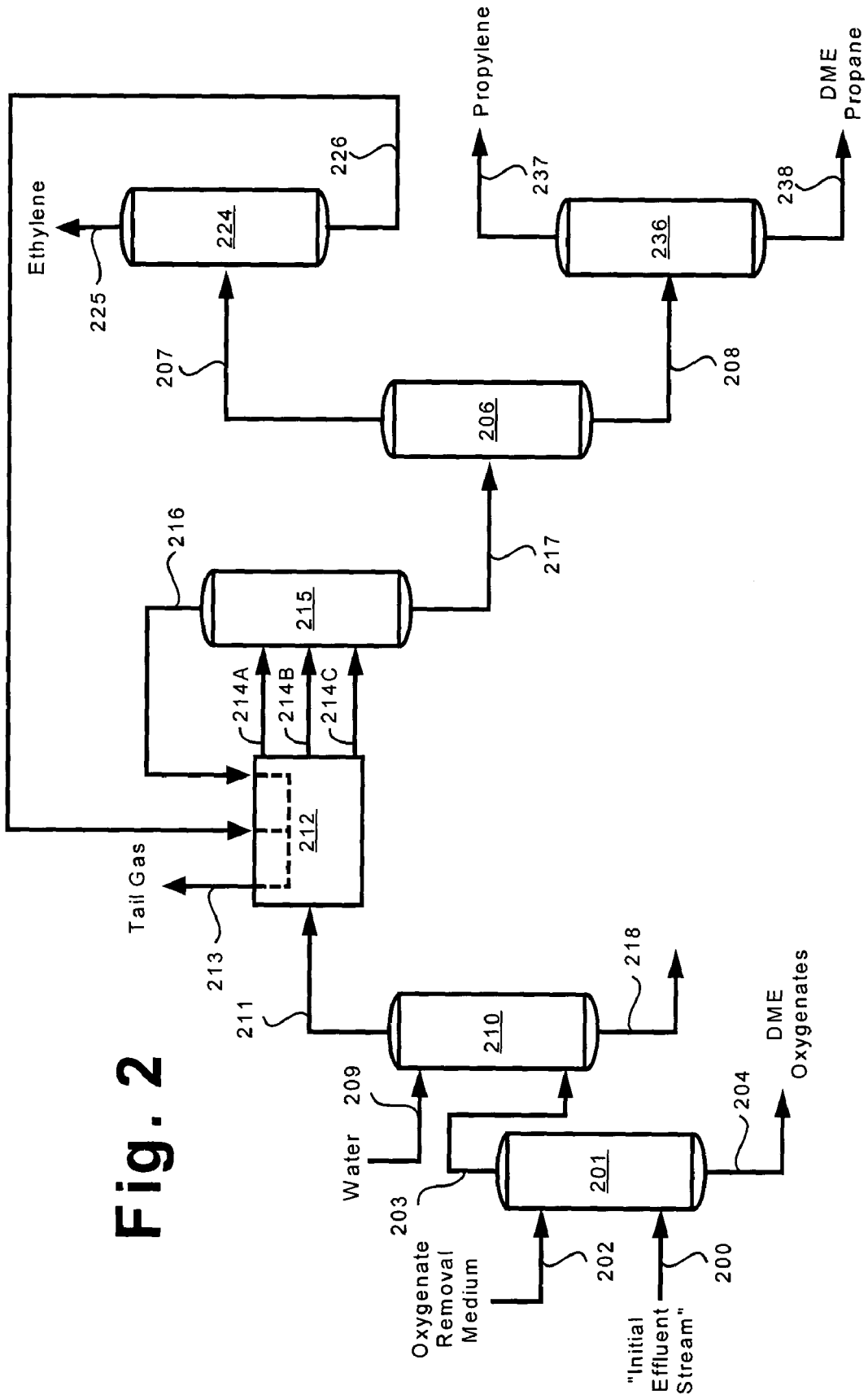
FIG. 2 illustrates a separation scheme according to another embodiment of the present invention.

As indicated above, "initial effluent stream," is defined herein as a stream containing dimethyl ether (DME), ethane, ethylene and propylene. Thus any of the following streams can be characterized as the initial effluent stream according to the present invention: the olefin-containing stream 302, quench overhead stream 306, compressed stream 308 or C3− stream 310. That is, any of these streams, preferably compressed stream 308 or C3− stream 310, optionally is the initial effluent stream 100/200 that is directed to the first separation unit 101/201 and processed as shown in FIG. 1 and FIG. 2, and as described in detail below.

The composition of the initial effluent stream will now be described. The initial effluent stream contains ethane, ethylene, propylene and DME. In one embodiment of the exemplary separation process, the initial effluent stream that is provided comprises not greater than about 50 weight percent DME, not greater than about 20 weight percent DME, not greater than about 10 weight percent DME, or not greater than about 5 weight percent DME. Of course, for DME to be removed from the initial effluent stream, some measurable amount must be present. Optionally, the provided initial effluent stream contains at least about 100 wppm DME, at least about 500 wppm DME, or at least about 1,000 wppm DME. If the initial effluent stream is derived from an OTO or MTO reaction system, the DME concentration in the initial effluent stream may be considerably higher, particularly if the OTO reaction system operates at an oxygenate conversion percentage of between about 93 weight percent and about 96 weight percent, based on the total weight of the oxygenate fed to the hydrocarbon conversion apparatus. In this embodiment, the initial effluent stream optionally contains more than 1000 wppm, more than 1500 wppm, more than 3000 wppm or more than 6000 wppm DME. DME levels optionally can be greater than 1.0, 2.0 or 3.0 weight percent DME, based on the total weight of the initial effluent stream. As used herein, "weight percent," "wppm" and "wppb" are based on the total weight of all components in a specified stream. Similarly, "volume percent," "vppm" and "vppb" are based on the total volume of all components in a specified stream.

In another embodiment of the inventive process, the initial effluent stream that is provided comprises at least about 25 weight percent ethylene. Preferably, the provided initial effluent stream comprises from about 25 weight percent ethylene to about 75 weight percent ethylene, more preferably from about 30 weight percent to about 60 weight percent, and most preferably from about 35 weight percent to about 50 weight percent ethylene. In terms of lower range limitations, the initial effluent stream optionally comprises at least about 5 weight percent, at least about 10 weight percent, or at least about 20 weight percent ethylene.

In another embodiment, the initial effluent stream that is provided also comprises at least about 20 weight percent propylene. Preferably, the provided initial effluent stream comprises from about 20 weight percent propylene to about 70 weight percent propylene, more preferably from about 25 weight percent to about 50 weight percent propylene, and most preferably from about 30 weight percent to about 40 weight percent propylene. In terms of lower range limitations, the initial effluent stream preferably comprises at least about 5 weight percent, more preferably at least about 10 weight percent, and most preferably at least about 15 weight percent propylene.

In another embodiment of the DME removal process, the initial effluent stream contains both ethylene and propylene. Desirably, the initial effluent stream contains at least about 50 weight percent ethylene and propylene. Preferably, the initial effluent stream contains from about 50 weight percent to about 95 weight percent ethylene and propylene, more preferably from about 55 weight percent to about 90 weight percent ethylene and propylene, and most preferably from about 60 weight percent to about 85 weight percent ethylene and propylene.

It is desirable that the provided initial effluent stream contains a relatively low concentration of ethane, preferably a lower concentration of ethane than propane. Preferably, the initial effluent stream comprises not greater than about 4 weight percent ethane, more preferably not greater than about 3 weight percent ethane, and most preferably not greater than about 2 weight percent ethane. In terms of lower range limitations, the initial effluent stream comprises at least about 0.1 weight percent, at least about 0.5 weight percent, or at least about 1.0 weight percent ethane.

It is also desirable that the initial effluent stream contains a relatively low concentration of propane, if any. Preferably, the initial effluent stream comprises not greater than about 5 weight percent propane, not greater than about 4 weight percent propane, or not greater than about 3 weight percent propane. In terms of lower range limitations, the initial effluent stream optionally contains at least about 0.1 weight percent, at least about 0.5 weight percent, or at least about 1.0 weight percent propane.

The initial effluent stream also optionally contains one or more of acetylene, and C$_4$+ components. If the initial effluent stream contains acetylene, the initial effluent stream optionally contains less than about 150 wppm, less than 100 wppm, less than 50 wppm, less than about 10 wppm, or less than about 1.0 wppm acetylene. In terms of lower range limitations, the initial effluent stream optionally contains at least about 0.1 wppm, at least about 0.5 wppm, or at least about 1.0 wppm acetylene. The initial effluent stream to be processed according to the present invention optionally is depleted in C$_4$+ hydrocarbons and C$_4$+ olefins (C$_4$+ components, collectively). The initial effluent stream preferably contains less than about 30 weight percent, more preferably less than about 20 weight percent, and most preferably less than about 15 weight percent C$_4$+ components. In terms of lower range limitations, the initial effluent stream optionally contains at least about 1 weight percent, at least about 5 weight percent, or at least about 10 weight percent C$_4$+ components. The initial effluent stream optionally contains less than about 10 weight percent, less than about 5 weight percent, or less than about 1 weight percent C$_4$+ olefins. The initial effluent stream optionally contains less than about 1.0 weight percent, less than about 0.5 weight percent, or less than about 0.1 weight percent C$_4$+ hydrocarbons.

Additionally, the initial effluent stream may include a minor amount of other components such as methyl acetylene, propadiene, and light ends. As used herein, "light ends" means components having a normal boiling point less than about −166° F. (−110° C.) and carbon monoxide. An exemplary list of light ends includes methane, carbon monoxide and hydrogen. The initial effluent stream to be processed according to the present invention optionally contains less than about 1.0 weight percent, less than about 0.5 weight percent, or less than about 0.01 weight percent light ends. The initial effluent stream optionally contains less than about 1.0 weight percent, less than about 0.5 weight percent, or less than about 0.1 weight percent methane. In terms of lower range limitations, the initial effluent stream optionally contains at least about 0.001 weight percent, at least 0.005 weight percent, at least 0.01 or at least 0.10 weight percent light ends. The initial effluent stream optionally contains at least about 0.001 weight percent, at least 0.005 weight percent, at least 0.01 or at least 0.10 weight percent methane. The initial effluent stream optionally contains less than about 0.01 weight percent, less than about 0.005 weight percent, or less than about 0.001 weight percent carbon monoxide. In terms of lower range limitations, the initial effluent stream optionally contains at least about 0.0001 weight percent, at least 0.0005 weight percent, at least about 0.001 or at least about 0.01 weight percent carbon monoxide.

The provided initial effluent stream can also contain some amount of water. Water that is present in the provided initial effluent stream should be at a concentration sufficiently low such that a separate water phase is not formed during the separation process. This is particularly important when a distillation column having trays is used in the inventive process, since a separate water phase formed in the trays will impede mass transfer and add extra weight to each tray. Distillation columns having packing are preferred at higher concentrations of water, since such a column will not have trays to hold up separate water phases. The initial effluent stream can contain some water. Optionally, the provided initial effluent stream contains not greater than about 15,000 wppm water, not greater than about 10,000 wppm water, not greater than 5,000 wppm water, or not greater than about 1,000 wppm water. The initial effluent stream optionally contains at least about 10 wppm water, at least about 20 wppm water, at least about 25 wppm water, at least about 100 wppm water, or at least about 200 wppm water.

Oxygenate Removal Medium Wash and Water Wash Steps

In one embodiment of the present invention, the initial effluent stream contacts an oxygenate removal medium in a first separation unit in order remove some, preferably a majority, of the non-DME oxygenate components contained therein. A non-limiting list of non-DME oxygenate components that may be present in the initial effluent stream includes: methyl ethyl ether, ethanol, isopropanol, acetic acid, propionic acid, ethanal, butanal, propanal, acetone, 2-butanone, 2-pentanone, 4-methyl-2-pentanone and methyl acetate. The resulting oxygenate depleted stream (which preferably contains some amount of DME) is then directed to a water wash unit, wherein residual oxygenate removal medium and additional non-DME oxygenates are removed therefrom. The remaining components in the resulting water washed oxygenate depleted stream are then separated preferably with a plurality of separation devices, e.g., distillation columns, as discussed in detail below.

According to one embodiment of the present invention, a first stream, e.g., the initial effluent stream, comprising DME, ethane, ethylene and propylene is directed to a first separation unit. The first separation unit preferably is a wash column designed to form a first overhead stream comprising the ethane, ethylene, propylene, and optionally propane and/or acetylene, and a first bottoms stream comprising a majority of the non-DME oxygenates and at least a portion of the DME. Optionally, a majority of the DME is yielded from the first separation unit to the first overhead stream.

A non-limiting list of exemplary oxygenate removal mediums includes alcohols, amines, amides, nitrites, heterocyclic nitrogen containing compounds, or a combination of any of the preceding. Either monohydric alcohols or polyhydric alcohols can be used as the oxygenate removal medium. Specific examples of oxygenate removal mediums include methanol, ethanol, propanol, ethylene glycol, diethylene glycol, tri(ethylene glycol), ethanolamine, diethanolamine, triethanolamine, hindered cyclic amines, acetonitrile, n-methylpyrrolidone, dimethyl formamide, and combinations thereof.

To obtain a substantial degree of effectiveness, the oxygenate removal medium optionally contains few non-oxygenate absorbing components. For example, the oxygenate removal medium optionally contains at least about 25, 50 or 75 weight percent oxygenate removal medium components. Optionally, the oxygenate removal medium contains at least about 90 weight percent, at least about 95 weight percent, or at least about 98 weight percent oxygenate removal medium. Lower oxygenate removal medium concentrations may be preferred if the oxygenate removal medium comprises an amine such as diethanolamine or acetyl-nitrile.

In one embodiment of the invention, the oxygenate removal medium is added to the first separation unit in an amount sufficient to substantially reduce non-DME oxygenate content. It is preferred that the oxygenate removal medium be added to the vessel at a molar ratio of oxygenate removal medium to total initial effluent stream entering the separation vessel of from about 4:1 to about 1:5,000. Preferably, the oxygenate removal medium is added at a molar ratio of oxygenate removal medium to total initial effluent stream of from about 1:2 to about 1:200, from about 1:5 to about 1:100, from about 1:7 to about 1:50, from about 1:7 to about 1:15, or about 1:10. Higher molar ratios of oxygenate removal medium to total initial effluent stream are desirable for reducing non-DME oxygenate content; preferably from about 4:1 to about 1:1, more preferably from about 3:1 to about 1.2:1, and most preferably from about 2.5:1 to about 1.5:1.

The oxygenate removal medium flow rate to the first separation unit optionally is from about 500 lb-moles/hr (227 kg-moles/hr) to about 2400 lb-moles/hr (1089 kg-moles/hr), from about 800 lb-moles/hr (363 kg-moles/hr) to about 2100 lb-moles/hr (953 kg-moles/hr), or from about 1000 lb-moles/hr (454 kg-moles/hr) to about 2000 lb-moles/hr (907 kg-moles/hr). Preferably the oxygenate removal medium flow rate is about 1800 lb moles/hr (816 kg-moles/hr).

If the initial effluent stream is washed with enough oxygenate removal medium, a majority of the DME will be removed therefrom with the bottoms stream. It is preferred, however, that a majority of the DME exit the first separation unit with the overhead stream. The residual DME in the overhead stream optionally is removed in additional downstream processing steps, such as in the propylene/propane separation step, described in detail below. In order to allow a majority of the DME to exit the first separation unit via the overhead stream, lower molar ratios of oxygenate removal medium to total initial effluent stream optionally are desirable. That is, the oxygenate removal medium ideally is not added to the separation vessel at a rate that removes a majority or all DME from the initial effluent stream. The molar ratio of oxygenate removal medium to total initial effluent stream preferably is less than about 1:20, less than about 1:100 or less than about 1:1000. Preferably, the molar ratio is from about 1:1 to about 1:5,000, more preferably from about 1:100 to about 1:4,000, and most preferably from about 1:500 to about 1:3,000. The molar ratio of oxygenate removal medium to DME (in the initial effluent stream) fed to the wash unit preferably is from about 1:1 to about 4:1, from about 1.3:1 to about 3:1, from about 1.5:1 to about 2:1, and most preferably about 1.8:1.

The first overhead stream from the first separation unit preferably is directed to a second separation unit, e.g., a water wash unit, for removal of residual oxygenate removal medium and additional non-DME oxygenates contained in the first overhead stream. In the second separation unit, the first overhead stream or a portion thereof contacts water under conditions effective to form a second overhead stream and a second bottoms stream. The second bottoms stream preferably contains a majority, by weight, of the residual oxygenate removal medium that was present in the first overhead stream. Ideally, the second bottoms stream contains more than 30 weight percent, more than 40 weight percent, or more that 60 weight percent of the oxygenate removal medium that was present in the first overhead stream.

In the second separation unit, it is preferred that the water be added to the vessel at a molar ratio of water to effluent entering the separation vessel of about 4:1 to about 1:5,000. Higher molar ratios of water to effluent received in the vessel are desirable for reducing oxygenate removal medium content as well as other oxygenates; preferably from about 1:5 to about 1:40, more preferably from about 1:10 to about 1:30, and most preferably from about 1:15 to about 1:20. Lower molar ratios of water to total effluent received optionally may be used. The molar ratio optionally is from about 1:1 to about 1:200, more preferably from about 1:10 to about 1:100, and most preferably from about 1:20 to about 1:300.

Preferably, the second overhead stream, or a stream derived therefrom, is directed to a caustic wash unit for removal of entrained acid gases such as CO2. Thus, the caustic wash unit removes CO2 from the second overhead stream, or from a portion thereof, and forms a CO2 depleted stream. The second overhead stream preferably contains relatively few hydrocarbon components that cause fouling problems in such acid gas treatment systems.

Solid or liquid acid gas treatment systems can be used in this invention. In either system, the acid gas is removed from the wash overhead stream or a stream derived therefrom by contacting the stream with an acid gas absorbent or adsorbent. Examples of such absorbents or adsorbents include amines, potassium carbonate, caustic, alumina, molecular sieves, and membranes, particularly membranes formed of polysulfone, polyimid, polyamide, glassy polymer and cellulose acetate. Solutions containing amines and caustic compounds are preferred, with caustic compounds being more preferred.

Aqueous amine solutions that are useful in this invention can contain any amine compound or compounds suitable for acid gas absorption. Examples include alkanolamines, such as triethanolamine (TEA); methyldiethanolamine (MDEA); diethanolamine (DEA); monoethanolamine (MEA); diisopropanolamine (DIPA); and hydroxyaminoethyl ether (DGA). Effective concentrations can range from about 0.5 to about 8 moles of amine per liter of aqueous solution.

Piperazine and/or monomethylethanolamine (MMEA) can be added to aqueous amine solutions to enhance their absorption capabilities. These additives can be included in the aqueous solution at a concentration of from about 0.04 to about 2 moles per liter of aqueous solution.

Caustic compounds that can be used in this invention are alkaline compounds, which are effective in removing acid gas from an initial effluent stream. Examples of such alkaline compounds include sodium hydroxide and potassium hydroxide.

This invention further includes an optional drying embodiment. In this embodiment, a solid or liquid drying system can be used to remove water and/or additional oxygenated hydrocarbons from the effluent stream that is directed thereto, e.g., water washed stream or a derivative thereof such as the CO2 depleted stream.

In the solid drying system, the effluent stream is received in a drying unit. In the drying unit, the effluent stream contacts a solid adsorbent to further remove water and oxygenated hydrocarbons to very low levels (excluding DME). Typically, the adsorption process is carried out in one or more fixed beds containing a suitable solid adsorbent.

Adsorption is useful for removing water and oxygenated hydrocarbons to very low concentrations, and for removing oxygenated hydrocarbons that are not normally removed by using other treatment systems. Preferably, an adsorbent system used as part of this invention has multiple adsorbent beds. Multiple beds allow for continuous separation without the need for shutting down the process to regenerate the solid adsorbent. For example, in a three bed system typically one bed is on-line, one bed is regenerated off-line, and a third bed is on stand-by.

The specific adsorbent solid or solids used in the adsorbent beds depends on the types of contaminants being removed. Examples of solid adsorbents for removing water and various polar organic compounds, such as oxygenated hydrocarbons and absorbent liquids, include aluminas, silica, 3Å molecular sieves, 4Å molecular sieves, and alumino-silicates. Beds containing mixtures of these sieves or multiple beds having different adsorbent solids can be used to remove water, as well as a variety of oxygenated hydrocarbons.

In this separation technique, one or more adsorption beds can be arranged in series or parallel. In one example of a series arrangement, a first bed is used to remove the smallest and most polar molecules, which are the easiest to remove. Subsequent beds for removing larger less polar oxygenated species are next in series. As a specific example of one type of arrangement, water is first selectively removed using a 3Å molecular sieve. This bed is then followed by one or more beds containing one or more less selective adsorbents such as a larger pore molecular sieve, e.g., 13×and/or a high surface area active alumina such as Selexorb CD (Alcoa tradename).

In another embodiment, the first bed is a 3.6Å molecular sieve capable of selectively removing both water and methanol. This bed can then be followed by one or more 13×or active alumina beds as described above.

The adsorbent beds can be operated at ambient temperature or at elevated temperature as required, and with either upward or downward flow. Regeneration of the adsorbent materials can be carried out by conventional methods including treatment with a stream of a dry inert gas such as nitrogen at elevated temperature.

In the liquid drying system, a water absorbent is used to remove water from the effluent stream received therein. The water absorbent can be any liquid effective in removing water from an olefin-containing stream. Preferably, the water absorbent is the same as that previously described.

The drying system of the present invention, whether employing a liquid or a solid drying agent, ideally forms a "dry stream," defined herein as a stream having a dew point of less than −40° F. (−40° C.). Preferably the dry stream from the drying unit has a dew point of less than −40° F. (−40° C.), more preferably less than about −60° F. (−51° C.), and most preferably less than −90° F. (−67.8° C.). The dry stream preferably is then directed to a separation system for removal of the remaining components contained therein, as described in more detail below.

C2/C3 Separation Followed by Light Ends Removal

In one embodiment of the present invention, C2/C3 separation is followed by light ends removal. In this embodiment, the second overhead stream, or a portion thereof, optionally after having been treated in an acid gas treating system and/or a drying unit, is directed to a third separation unit, e.g., a C2/C3 splitter, for further processing. The third separation unit preferably subjects the second overhead stream from the second separation unit to conditions, e.g., temperature and pressure, that are effective to separate the second overhead stream into a third overhead stream and a third bottoms stream. The third overhead stream contains a majority of the ethane and ethylene, individually or collectively, that was present in the second overhead stream. More preferably, the third overhead stream comprises at least about 60 weight percent, more preferably at least about 75 weight percent, and most preferably at least about 90 weight percent of the ethane and ethylene, individually or collectively, that was present in the second overhead stream from the second separation unit. If the second overhead stream includes acetylene, then the third overhead stream preferably contains a majority of the acetylene that was present in the second overhead stream. More preferably, the third overhead stream comprises at least about 60 weight percent, more preferably at least about 75 weight percent, and most preferably at least about 90 weight percent of the acetylene that was present in the second overhead stream.

The third bottoms stream contains a majority of the propylene that was present in the second overhead stream. More preferably, the third bottoms stream comprises at least about 60 weight percent, more preferably at least about 75 weight percent, and most preferably at least about 90 weight percent of the propylene that was present in the second overhead stream. If the second overhead stream includes propane, then the third bottoms stream preferably contains a majority of the propane that was present in the second overhead stream. More preferably, the third bottoms stream comprises at least about 60 weight percent, more preferably at least about 75 weight percent, and most preferably at least about 90 weight percent of the propane that was present in the second overhead stream. If the second overhead stream includes DME, as is preferred, then the third bottoms stream preferably contains a majority of the DME that was present in the second overhead stream. More preferably, the third bottoms stream comprises at least about 60 weight percent, more preferably at least about 85 weight percent, and most preferably at least about 99.9 weight percent of the DME that was present in the second overhead stream. The third separation unit preferably includes one or more distillation and/or fractionation columns, absorbers and/or extractive distillation columns that are designed to form one or more overhead streams comprising ethane and ethylene, and optionally acetylene, and one or more bottoms streams comprising propylene, and optionally DME and propane.

If the initial effluent stream contains light ends such as methane, carbon monoxide and hydrogen, then the third overhead stream (which will contain a majority of the light ends from the initial effluent stream via the first and second overhead streams) preferably is directed to a fourth separation unit, e.g., a light ends removal unit, for further processing. The fourth separation unit preferably subjects the third overhead stream or a portion thereof to conditions, e.g., temperature and pressure, that are effective to separate the third overhead stream into a fourth overhead stream and a fourth bottoms stream. The fourth overhead stream contains a majority of the light ends, individually or collectively, that were present in the third overhead stream. More preferably, the fourth overhead stream comprises at least about 60 weight percent, more preferably at least about 75 weight percent, and most preferably at least about 90 weight percent of the light ends, individually or collectively, that were present in the third overhead stream. The fourth bottoms stream contains a majority of the ethane and ethylene, individually or collectively, that were present in the third overhead stream. More preferably, the fourth bottoms stream comprises at least about 60 weight percent, more preferably at least about 75 weight percent, and most preferably at least about 90 weight percent of the ethane and ethylene, individually or collectively, that were present in the third overhead stream. The fourth separation unit preferably includes one or more distillation and/or fractionation columns, absorbers and/or extractive distillation columns that are designed to form one or more overhead streams comprising methane and any other light ends, and one or more bottoms streams comprising ethane and ethylene.

Preferably, the fourth bottoms stream is directed to a fifth separation unit, e.g., a C2 splitter, for further processing. The fifth separation unit preferably subjects the fourth bottoms stream to conditions, e.g., temperature and pressure, that are effective to separate the fourth bottoms stream into a fifth overhead stream and a fifth bottoms stream. The fifth overhead stream contains a majority of the ethylene that was present in the fourth bottoms stream. More preferably, the fifth overhead stream comprises at least about 60 weight percent, more preferably at least about 75 weight percent, and most preferably at least about 90 weight percent of the ethylene that was present in the fourth bottoms stream. The fifth bottoms stream contains a majority of the ethane that was present in the fourth bottoms stream. More preferably, the fifth bottoms stream comprises at least about 60 weight percent, more preferably at least about 75 weight percent, and most preferably at least about 90 weight percent of the ethane that was present in the fourth bottoms stream. The fifth separation unit preferably includes one or more distillation and/or fractionation columns, absorbers and/or extractive distillation columns that are designed to form one or more overhead streams comprising polymerization grade ethylene, and one or more bottoms streams comprising ethane.

Depending on the amount of propane and DME present in the initial effluent stream, the third bottoms stream may contain propylene suitable for polymerization. Optionally, the third bottoms stream from the third separation unit is directed to a sixth separation unit, e.g., a C3 splitter, for additional propane and DME removal. The sixth separation unit preferably subjects the third bottoms stream or a portion thereof to conditions, e.g., temperature and pressure, that are effective to separate the third bottoms stream into a sixth overhead stream and a sixth bottoms stream. The sixth overhead stream contains a majority of the propylene that was present in the third bottoms stream. More preferably, the sixth overhead stream comprises at least about 60 weight percent, more preferably at least about 75 weight percent, and most preferably at least about 90 weight percent of the propylene that was present in the third bottoms stream. The sixth bottoms stream contains a majority of the propane, if any, that was present in the third bottoms stream. More preferably, the sixth bottoms stream comprises at least about 60 weight percent, more preferably at least about 75 weight percent, and most preferably at least about 90 weight percent of the propane, if any, that was present in the third bottoms stream. The sixth bottoms stream also contains a majority of the DME that was present in the third bottoms stream. More preferably, the sixth bottoms stream comprises at least about 60 weight percent, more preferably at least about 85 weight percent, and most preferably at least about 99.9 weight percent of the DME, if any, that was present in the third bottoms stream. The sixth separation unit preferably includes one or more distillation and/or fractionation columns, absorbers and/or extractive distillation columns that are designed to form one or more overhead streams comprising polymerization grade propylene, and one or more bottoms streams comprising propane, if any was present in the third bottoms stream, and DME. The sixth bottoms stream provides an ideal fuel for various fuel requiring processes within the reaction system.

DME is particularly difficult to remove from the initial effluent stream. One preferred embodiment of the invention includes removing DME from the initial effluent stream in a plurality of steps (preferably in two steps). In this embodiment, the first separation unit, described above, removes a first portion of DME, preferably a minority of the DME, from the initial effluent stream in the first bottoms stream. A second portion of the DME from the initial effluent stream remains in the first overhead stream. Thus, both the first overhead stream and the first bottoms stream contain a detectable amount of DME. In terms of lower range limitations, the first overhead stream optionally includes at least about 60 weight percent, at least about 75 weight percent, at least about 90 weight percent, or at least about 95 weight percent of the DME that was present in the initial effluent stream. The first bottoms stream optionally includes at least about 5 weight percent, at least about 10 weight percent, at least about 15 weight percent, or at least about 30 weight percent of the DME that was present in the initial effluent stream. In one embodiment, the first bottoms stream contains from about 2 weight percent to about 50 weight percent, more preferably from about 5 to about 15 weight percent, and most preferably from about 5 to about 10 weight percent of the DME that was present in the initial effluent stream.

The DME remaining in the first overhead stream then passes through the second separation unit, the third separation unit and the sixth separation unit via the second overhead stream and the third bottoms stream. Ultimately, a C3 split is made between propylene and propane in the sixth separation unit separating the third bottoms stream into the sixth overhead stream containing a majority of the propylene that was present in the third bottoms stream, and the sixth bottoms stream containing a majority of the propane and DME that was present in the third bottoms stream. Thus, the first separation unit and the sixth separation unit act to remove DME. The sixth bottoms stream from the sixth separation unit preferably contains from about 60 weight percent to about 90 weight percent, more preferably from about 65 to about 85 weight percent, and most preferably from about 70 to about 80 weight percent of the DME that was present in the initial effluent stream.

The two step DME removal process of the present invention is expressed well in terms of the ratio of DME removed, by mole, in the first separation unit (e.g., the oxygenate removal medium wash unit) to DME removed, by mole, in the bottoms stream from the separation unit making the C3 split (e.g., the sixth separation unit). Optionally, the ratio is at least 1:1, at least 1:2 or at least 1:3. In terms of ranges, the ratio optionally is from about 1:1 to about 1:20, from about 1:2 to about 1:15, or from about 1:3 to about 1:10.

Acetylene and other multiply unsaturated species are generally undesirable compounds, which preferably are converted to a more desirable form in one or more hydrogenation converters, e.g., acetylene converters. The hydrogenation converters are adapted to at least partially saturate acetylene or other multiply unsaturated species to, for example, alkenes and/or alkanes. Specifically, in a hydrogenation converter, multiply unsaturated species such as acetylene contact hydrogen and/or carbon monoxide under conditions effective to at least partially hydrogenate the multiply unsaturated species. The one or more acetylene converters may be adapted to at least partially hydrogenate other components as well. A non-limiting list of other exemplary components that may be at least partially hydrogenated in a hydrogenation converter includes: acetylene, methyl acetylene and propadiene. Preferably, the hydrogenation converter converts acetylene to ethylene; methyl acetylene to propylene; and propadiene to propylene. Desirable components such as ethylene and propylene preferably pass through the one or more hydrogenation converters unaltered. According to the present invention, the one or more hydrogenation converters may be oriented in a variety of locations, although the converters ideally are oriented along one or more streams that contain acetylene, methyl acetylene and/or propadiene. In the separation sequence described above, the one or more hydrogenation converters preferably receive and processes multiply unsaturated species from the second overhead stream, the third overhead stream, the third bottoms stream or the fourth bottoms stream, as these fractions contain the highest concentrations of acetylene, methyl acetylene, and/or propadiene.

FIG. 1 illustrates this embodiment of the present invention. As shown, initial effluent stream 100, which contains ethane, ethylene, DME, propane, and propylene is directed to first separation unit 101, which preferably is a wash column adapted to remove a majority of the non-DME oxygenates from the initial effluent stream 100. In the first separation unit 101, the initial effluent stream 100 contacts an oxygenate removal medium 102, preferably methanol, under conditions effective to remove some of the oxygenates therefrom. This means that ethane, ethylene, propane, propylene and at least some of the DME are recoverable in a first overhead stream 103, with the bulk of the oxygenate removal medium 102, non-DME oxygenates and at least some of the DME being recoverable in a first bottoms stream 104. The first overhead stream 103 also likely contains a minor amount of residual oxygenate removal medium. The first separation unit 101 optionally includes a reflux line and/or a reboiler line and corresponding heat exchangers, not shown, to facilitate separation of these components.

First overhead stream 103 is then directed to a second separation unit 110, which preferably is a water wash column adapted to separate any residual oxygenate removal medium 102 carried over from the first separation unit 101 via first overhead stream 103. Specifically, in second separation unit 110, the first overhead stream 103 contacts water 109 under conditions effective to remove at least a majority of the residual oxygenate removal medium therefrom. Thus, ethane, ethylene, propane, propylene and DME from the first overhead stream 103 are recoverable in a second overhead stream 111, with the bulk of the residual oxygenate removal medium 102 and water 109 being recoverable in a second bottoms stream 118. The second separation unit 110 optionally includes a reflux line and/or a reboiler line and corresponding heat exchangers, not shown, to facilitate separation of these components.

Optionally, second overhead stream 111 is directed to a caustic wash unit, not shown, to remove carbon dioxide, and/or a drying unit, not shown. Reverting to FIG. 1, second overhead stream 111 preferably is directed to a third separation unit 106. The third separation unit 106 preferably is a distillation column adapted to separate C2– components from C3+ components. Specifically, the third separation unit 106 separates the second overhead stream 111 into a third overhead stream 107, which contains a majority of the ethane and ethylene that was present in the second overhead stream 111, and a third bottoms stream 108, which preferably contains a majority of the propane, DME and propylene that was present in the second overhead stream 111. The third separation unit 106 optionally includes a reflux line and/or a reboiler line and corresponding heat exchangers, not shown, to facilitate separation of the C2– components from the C3+ components.

Third overhead stream 107 preferably is introduced into demethanizer feed train 112. Demethanizer feed train 112 is a "cold box" that preferably is formed of a series of coolers, e.g., Core Exchangers, and knock out drums, not shown, that cool third overhead stream 107 and form a plurality of cooled streams 114A–C. Cooled streams 114A–C may be in liquid and/or vapor form. Preferably, cooled streams 114A–C are directed to a fourth separation unit 115 for further processing. The fourth separation unit 115 preferably is a distillation column adapted to separate light ends such as methane, hydrogen and/or carbon monoxide from ethane and ethylene. Specifically, the fourth separation unit 115 separates the cooled streams 114A–C, collectively, into a fourth overhead stream 116, which contains a majority of the light ends that were present in the cooled streams 114A–C, and a fourth bottoms stream 117, which preferably contains a majority of the ethane and ethylene that was present in the cooled streams 114A–C. The fourth separation unit 115 optionally includes a reflux line and/or a reboiler line and corresponding heat exchangers, not shown, to facilitate separation of the light ends from ethane and ethylene. In one embodiment, the fourth overhead stream 116 is directed to the demethanizer feed train 112 for use as a cooling medium.

The fourth bottoms stream 117 is directed to a fifth separation unit 124 for further processing. The fifth separation unit 124 preferably is a distillation column adapted to separate ethylene from ethane. Specifically, the fifth separation unit 124 separates the fourth bottoms stream 117 into a fifth overhead stream 125, which contains a majority of the ethylene that was present in the fourth bottoms stream 117, and a fifth bottoms stream 126, which preferably contains a majority of the ethane that was present in the fourth bottoms stream 117. The fifth separation unit 124 optionally includes a reflux line and/or a reboiler line and corresponding heat exchangers, not shown, to facilitate separation of ethylene from ethane. Fifth overhead stream 125 contains relatively pure ethylene, which may be directed to a polymerization unit, not shown, for polymerization. The fifth bottoms stream 126 preferably is directed to the demethanizer feed train 112 for use as a cooling medium. Optionally, the fifth bottoms stream 126 is combined with the cooling medium from fourth overhead stream 116, as shown by the broken line in demethanizer feed train 112. After cooling the vapor from third overhead stream 107 in the demethanizer feed train 112, the cooling mediums exit the demethanizer feed train 112 through tail gas line 113.

If the initial effluent stream was depleted in $C_4+$ components, then the third bottoms stream 108 may, depending on the amount of propane and DME in the initial effluent stream, contain mostly propylene and a minor amount of DME and propane, and may be well-suited for polymerization disposition. If very high quality propylene is desired, then the third bottoms stream 108 optionally is introduced into sixth separation unit 136. The sixth separation unit 136 preferably is a distillation column adapted to separate propylene from propane and DME. The sixth separation unit 136 thus may operate as a C3 splitter. Specifically, the sixth separation unit 136 separates the third bottoms stream 108 into a sixth overhead stream 137, which contains a majority of the propylene that was present in the third bottoms stream 108, and a sixth bottoms stream 138, which preferably contains a majority of the propane, DME and optionally any residual $C_4+$ components that were present in the third bottoms stream 108. The sixth separation unit 136 optionally includes a reflux line and/or a reboiler line and corresponding heat exchangers, not shown, to facilitate separation of the propylene from the propane. The sixth overhead stream 137 contains very high quality propylene, which is suitable for polymerization. The sixth bottoms stream 138 preferably is burned as fuel or is directed to a DME recovery unit.

If the initial effluent stream 100 contains $C_4+$ components in any appreciable quantity, then the process flow scheme according to the present invention preferably includes a depropanizer, not shown. The depropanizer is adapted to separate $C_4+$ components from C3– components, e.g., light ends, ethylene, ethane, propylene, propane and DME. The placement of the depropanizer may vary widely. In the embodiment illustrated in FIG. 1, the depropanizer optionally receives and removes at least a majority of the $C_4+$ components from one or more of the following streams: the initial effluent stream 100, the second overhead stream 111, the third bottoms stream 108 or the sixth bottoms stream 138.

If the initial effluent stream 100 contains acetylene, methyl acetylene, propadiene, or other multiply unsaturated components, then the system of the present invention preferably includes a hydrogenation converter, e.g., an acetylene or MAPD converter, not shown. If incorporated into the present invention, the hydrogenation converter preferably receives and processes one or more of the following streams: the second overhead stream 111, the third overhead stream 107, the third bottoms stream 108 and/or the fourth bottoms stream 117. In the hydrogenation converter, acetylene contacts hydrogen and carbon dioxide under conditions effective to convert at least a portion of the acetylene to ethylene. Similarly, methyl acetylene and/or propadiene contact hydrogen and carbon dioxide under conditions effective to convert at least a portion of the methyl acetylene and/or propadiene to propylene. Components other than acetylene, methyl acetylene and propadiene that are present in the above-identified streams preferably pass unaltered through the hydrogenation converter(s). The resulting acetylene-depleted streams are then processed as described above with reference to FIG. 1.

Light Ends Removal Followed by C2/C3 Separation

In one embodiment of the present invention, light ends removal is followed by C2/C3 separation. In this embodiment, the second overhead stream, or a portion thereof, optionally after having been treated in an acid gas treating system and/or a drying unit, is directed to a third separation unit, e.g., a light ends removal unit, for further processing.

The third separation unit preferably subjects the second overhead stream or a portion thereof to conditions, e.g., temperature and pressure, that are effective to separate the second overhead stream into a third overhead stream and a third bottoms stream. The third overhead stream contains a majority of the light ends, individually or collectively, that were present in the second overhead stream. More preferably, the third overhead stream comprises at least about 60 weight percent, more preferably at least about 75 weight percent, and most preferably at least about 90 weight percent of the light ends, individually or collectively, that were present in the second overhead stream. The third bottoms stream contains a majority of the ethane, ethylene, propylene and DME, individually or collectively, that were present in the second overhead stream. More preferably, the third bottoms stream comprises at least about 60 weight percent, more preferably at least about 75 weight percent, and most preferably at least about 90 weight percent of the ethane, ethylene, propylene and DME, individually or collectively, that were present in the second overhead stream. The third separation unit preferably includes one or more distillation and/or fractionation columns, absorbers and/or extractive distillation columns that are designed to form one or more overhead streams comprising methane and any other light ends, and one or more bottoms streams comprising ethane, ethylene, propylene and DME. If the initial effluent stream, the first overhead stream and the second overhead stream contain propane and/or acetylene, the third overhead stream also preferably contains at least about 60 weight percent, more preferably at least about 75 weight percent, and most preferably at least about 90 weight percent of the propane and/or acetylene, individually or collectively, that was present in the second overhead stream.

In this embodiment, the third bottoms stream is directed to a fourth separation unit, e.g., a C2/C3 splitter, for further processing. The fourth separation unit preferably subjects the third bottoms stream from the third separation unit to conditions, e.g., temperature and pressure, that are effective to separate the third bottoms stream into a fourth overhead stream and a fourth bottoms stream. The fourth overhead stream contains a majority of the ethane and ethylene, individually or collectively, that was present in the third bottoms stream. More preferably, the fourth overhead stream comprises at least about 60 weight percent, more preferably at least about 75 weight percent, and most preferably at least about 90 weight percent of the ethane and ethylene, individually or collectively, that was present in the third bottoms stream from the third separation unit. If the third bottoms stream includes acetylene, then the fourth overhead stream preferably contains a majority of the acetylene that was present in the third bottoms stream. More preferably, the fourth overhead stream comprises at least about 60 weight percent, more preferably at least about 75 weight percent, and most preferably at least about 90 weight percent of the acetylene that was present in the third bottoms stream.

The fourth bottoms stream contains a majority of the propylene that was present in the second overhead stream. More preferably, the fourth bottoms stream comprises at least about 60 weight percent, more preferably at least about 75 weight percent, and most preferably at least about 90 weight percent of the propylene that was present in the third bottoms stream. If the third bottoms stream includes propane, then the fourth bottoms stream preferably contains a majority of the propane that was present in the third bottoms stream. More preferably, the fourth bottoms stream comprises at least about 60 weight percent, more preferably at least about 75 weight percent, and most preferably at least about 90 weight percent of the propane that was present in the third bottoms stream. If the third bottoms stream includes DME, as is preferred, then the fourth bottoms stream preferably contains a majority of the DME that was present in the third bottoms stream. More preferably, the fourth bottoms stream comprises at least about 60 weight percent, more preferably at least about 85 weight percent, and most preferably at least about 99.9 weight percent of the DME that was present in the third bottoms stream. The fourth separation unit preferably includes one or more distillation and/or fractionation columns, absorbers and/or extractive distillation columns that are designed to form one or more overhead streams comprising ethane and ethylene, and optionally acetylene, and one or more bottoms streams comprising propylene, and optionally DME and propane.

Preferably, the fourth overhead stream is directed to a fifth separation unit, e.g., a C2 splitter, for further processing. The fifth separation unit preferably subjects the fourth overhead stream to conditions, e.g., temperature and pressure, that are effective to separate the fourth overhead stream into a fifth overhead stream and a fifth bottoms stream. The fifth overhead stream contains a majority of the ethylene that was present in the fourth overhead stream. More preferably, the fifth overhead stream comprises at least about 60 weight percent, more preferably at least about 75 weight percent, and most preferably at least about 90 weight percent of the ethylene that was present in the fourth overhead stream. The fifth bottoms stream contains a majority of the ethane that was present in the fourth overhead stream. More preferably, the fifth bottoms stream comprises at least about 60 weight percent, more preferably at least about 75 weight percent, and most preferably at least about 90 weight percent of the ethane that was present in the fourth overhead stream. The fifth separation unit preferably includes one or more distillation and/or fractionation columns, absorbers and/or extractive distillation columns that are designed to form one or more overhead streams comprising polymerization grade ethylene, and one or more bottoms streams comprising ethane.

Depending on the amount of propane and DME present in the initial effluent stream, the fourth bottoms stream may contain propylene suitable for polymerization. Optionally, the fourth bottoms stream from the fourth separation unit is directed to a sixth separation unit, e.g., a C3 splitter, for propane and DME removal. The sixth separation unit preferably subjects the fourth bottoms stream or a portion thereof to conditions, e.g., temperature and pressure, that are effective to separate the fourth bottoms stream into a sixth overhead stream and a sixth bottoms stream. The sixth overhead stream contains a majority of the propylene that was present in the fourth bottoms stream. More preferably, the sixth overhead stream comprises at least about 60 weight percent, more preferably at least about 75 weight percent, and most preferably at least about 90 weight percent of the propylene that was present in the fourth bottoms stream. The sixth bottoms stream contains a majority of the propane, if any, that was present in the fourth bottoms stream. More preferably, the sixth bottoms stream comprises at least about 60 weight percent, more preferably at least about 75 weight percent, and most preferably at least about 90 weight percent of the propane, if any, that was present in the fourth bottoms stream. The sixth bottoms stream also contains a majority of the DME that was present in the fourth bottoms stream. More preferably, the sixth bottoms stream comprises at least about 60 weight percent, more preferably at least about 85 weight percent, and most preferably at least about 99.9 weight percent of the DME, if any, that was present in the fourth bottoms stream. The sixth separation unit preferably includes one or more distillation and/or fractionation columns, absorbers and/or extractive distillation columns that are designed to form one or more overhead streams comprising polymerization grade propylene, and one or more bottoms streams comprising propane, if any was present in the fourth bottoms stream, and DME. The sixth bottoms stream provides an ideal fuel for various fuel requiring processes within the reaction system.

As indicated above, DME is particularly difficult to remove from the initial effluent stream. One preferred embodiment of the invention includes removing DME from the initial effluent stream in a plurality of steps (preferably in two steps). In this embodiment, the first separation unit, described above, removes a first portion of DME, preferably a minority of the DME, from the initial effluent stream in the first bottoms stream. A second portion of the DME from the initial effluent stream remains in the first overhead stream. Thus, both the first overhead stream and the first bottoms stream contain a detectable amount of DME. In terms of lower range limitations, the first overhead stream optionally includes at least about 60 weight percent, at least about 75 weight percent, at least about 90 weight percent, or at least about 95 weight percent of the DME that was present in the initial effluent stream. The first bottoms stream optionally includes at least about 5 weight percent, at least about 10 weight percent, at least about 15 weight percent, or at least about 30 weight percent of the DME that was present in the initial effluent stream. In one embodiment, the first bottoms stream contains from about 2 weight percent to about 50 weight percent, more preferably from about 5 to about 15 weight percent, and most preferably from about 5 to about 10 weight percent of the DME that was present in the initial effluent stream.

The DME remaining in the first overhead stream then passes through the second separation unit, the third separation unit and the fourth separation unit via the second overhead stream and the third bottoms stream. Ultimately, a C3 split is made between propylene and propane in the sixth separation unit separating the fourth bottoms stream into the sixth overhead stream containing a majority of the propylene that was present in the fourth bottoms stream, and the sixth bottoms stream containing a majority of the propane and DME that was present in the fourth bottoms stream. Thus, the first separation unit and the sixth separation unit act to remove DME. The sixth bottoms stream from the sixth separation unit preferably contains from about 60 weight percent to about 99.9 weight percent, more preferably from about 75 to about 95 weight percent, and most preferably from about 80 to about 90 weight percent of the DME that was present in the initial effluent stream.

The two step DME removal process of the present invention is expressed well in terms of the ratio of DME removed, by mole, in the first separation unit (e.g., the oxygenate removal medium wash unit) to DME removed, by mole, in the bottoms stream from the separation unit making the C3 split (e.g., the sixth separation unit). Optionally, the ratio is at least 1:1, at least 1:2 or at least 1:3. In terms of ranges, the ratio optionally is from about 1:1 to about 1:20, from about 1:2 to about 1:15, or from about 1:3 to about 1:10.

Acetylene and other multiply unsaturated species are generally undesirable compounds, which preferably are converted to a more desirable form in one or more hydrogenation converters, e.g., acetylene converters. The hydrogenation converters are adapted to at least partially saturate acetylene or other multiply unsaturated species to, for example, alkenes and/or alkanes. Specifically, in a hydrogenation converter, multiply unsaturated species such as acetylene contact hydrogen and/or carbon monoxide under conditions effective to at least partially hydrogenate the multiply unsaturated species. The one or more acetylene converters may be adapted to at least partially hydrogenate other components as well. A non-limiting list of other exemplary components that may be at least partially hydrogenated in a hydrogenation converter includes: acetylene, methyl acetylene and propadiene. Preferably, the hydrogenation converter converts acetylene to ethylene; methyl acetylene to propylene; and propadiene to propylene. Desirable components such as ethylene and propylene preferably pass through the one or more hydrogenation converters unaltered. According to the present invention, the one or more hydrogenation converters may be oriented in a variety of locations, although the converters ideally are oriented along one or more streams that contain acetylene, methyl acetylene and/or propadiene. In the separation sequence described above, the one or more hydrogenation converters preferably receive and processes multiply unsaturated species from the second overhead stream, the third bottoms stream, the fourth overhead stream, or the fourth bottoms stream, as these fractions contain the highest concentrations of acetylene, methyl acetylene, and/or propadiene.

FIG. 2 illustrates this embodiment of the present invention. As shown, initial effluent stream 200, which contains ethane, ethylene, DME, propane, and propylene is directed to first separation unit 201, which preferably is a wash column adapted to remove a majority of the non-DME oxygenates from the initial effluent stream 200. In the first separation unit 201, the initial effluent stream 200 contacts an oxygenate removal medium 202, preferably methanol, under conditions effective to remove some of the oxygenates therefrom. This means that ethane, ethylene, propane, propylene and at least some of the DME are recoverable in a first overhead stream 203, with the bulk of the oxygenate removal medium 202, non-DME oxygenates and at least some of the DME being recoverable in a first bottoms stream 204. The first overhead stream 203 also likely contains a minor amount of residual oxygenate removal medium. The first separation unit 201 optionally includes a reflux line and/or a reboiler line and corresponding heat exchangers, not shown, to facilitate separation of these components.

First overhead stream 203 is then directed to a second separation unit 210, which preferably is a water wash column adapted to separate any residual oxygenate removal medium 202 carried over from the first separation unit 201 via first overhead stream 203. Specifically, in second separation unit 210, the first overhead stream 203 contacts water 209 under conditions effective to remove at least a majority of the residual oxygenate removal medium therefrom. Thus, ethane, ethylene, propane, propylene and DME from the first overhead stream 203 are recoverable in a second overhead stream 211, with the bulk of the residual oxygenate removal medium 202 and water 209 being recoverable in a second bottoms stream 218. The second separation unit 210 optionally includes a reflux line and/or a reboiler line and corresponding heat exchangers, not shown, to facilitate separation of these components.

Optionally, second overhead stream 211 is directed to a caustic wash unit, not shown, to remove carbon dioxide, and/or a drying unit, not shown. Reverting to FIG. 2, second overhead stream 211 preferably is directed to demethanizer feed train 212. Demethanizer feed train 212 is a "cold box" that preferably is formed of a series of coolers, e.g., Core Exchangers, and knock out drums, not shown, that cool second overhead stream 211 and form a plurality of cooled streams 214A–C. Cooled streams 214A–C may be in liquid and/or vapor form. Preferably, cooled streams 214A–C are directed to a third separation unit 215 for further processing. The third separation unit 215 preferably is a distillation column adapted to separate light ends such as methane, hydrogen and/or carbon monoxide from ethane, ethylene, propane, DME and propylene. Specifically, the third separation unit 215 separates the cooled streams 214A–C, collectively, into a third overhead stream 216, which contains a majority of the light ends that were present in the cooled streams 214A–C, and a third bottoms stream 217, which preferably contains a majority of the ethane, ethylene, propane, DME and propylene that was present in the cooled streams 214A–C. The third separation unit 215 optionally includes a reflux line and/or a reboiler line and corresponding heat exchangers, not shown, to facilitate separation of the light ends from ethane, ethylene, propane, DME and propylene. In one embodiment, the third overhead stream 216 is directed to the demethanizer feed train 212 for use as a cooling medium.

Third bottoms stream 217 preferably is introduced into a fourth separation unit 206. The fourth separation unit 206 preferably is a distillation column adapted to separate C2– components from C3+ components. Specifically, the fourth separation unit 206 separates the third bottoms stream 217 into a fourth overhead stream 207, which contains a majority of the ethane and ethylene that was present in the third bottoms stream 217, and a fourth bottoms stream 208, which preferably contains a majority of the propane, DME and propylene that was present in the third bottoms stream 217. The fourth separation unit 206 optionally includes a reflux line and/or a reboiler line and corresponding heat exchangers, not shown, to facilitate separation of the C2– components from the C3+ components.

The fourth overhead stream 207 is directed to a fifth separation unit 224 for further processing. The fifth separation unit 224 preferably is a distillation column adapted to separate ethylene from ethane. Specifically, the fifth separation unit 224 separates the fourth overhead stream 207 into a fifth overhead stream 225, which contains a majority of the ethylene that was present in the fourth overhead stream 207, and a fifth bottoms stream 226, which preferably contains a majority of the ethane that was present in the fourth overhead stream 207. The fifth separation unit 224 optionally includes a reflux line and/or a reboiler line and corresponding heat exchangers, not shown, to facilitate separation of ethylene from ethane. Fifth overhead stream 225 contains relatively pure ethylene, which may be directed to a polymerization unit, not shown, for polymerization. The fifth bottoms stream 226 preferably is directed to the demethanizer feed train 212 for use as a cooling medium. Optionally, the fifth bottoms stream 226 is combined with the cooling medium from third overhead stream 216, as shown by the broken line in demethanizer feed train 212. After cooling the vapor from second overhead stream 211 in the demethanizer feed train 212, the cooling mediums exit the demethanizer feed train 212 through tail gas line 213.

If the initial effluent stream was depleted in $C_4+$ components, then the fourth bottoms stream 208 may, depending on the amount of propane and DME in the initial effluent stream, contain mostly propylene and a minor amount of DME and propane, and may be well-suited for polymerization disposition. If very high quality propylene is desired, then the fourth bottoms stream 208 optionally is introduced into sixth separation unit 236. The sixth separation unit 236 preferably is a distillation column adapted to separate propylene from propane and DME. The sixth separation unit 236 thus may operate as a C3 splitter. Specifically, the sixth separation unit 236 separates the fourth bottoms stream 208 into a sixth overhead stream 237, which contains a majority of the propylene that was present in the fourth bottoms stream 208, and a sixth bottoms stream 238, which preferably contains a majority of the propane, DME and optionally any residual $C_4+$ components that were present in the fourth bottoms stream 208. The sixth separation unit 236 optionally includes a reflux line and/or a reboiler line and corresponding heat exchangers, not shown, to facilitate separation of the propylene from the propane. The sixth overhead stream 237 contains very high quality propylene, which is suitable for polymerization. The sixth bottoms stream 238 preferably is burned as fuel.

If the initial effluent stream contains $C_4+$ components in any appreciable quantity, then the process flow scheme according to the present invention preferably includes a depropanizer, not shown. The depropanizer is adapted to separate $C_4+$ components from C3– components, e.g., light ends, ethylene, ethane, propylene, propane and DME. The placement of the depropanizer may vary widely. In the embodiment illustrated in FIG. 2, the depropanizer optionally receives and removes at least a majority of the $C_4+$ components from one or more of the following streams: the initial effluent stream 200, the second overhead stream 211, the third bottoms stream 217, the fourth bottoms stream 208 or the sixth bottoms stream 238.

If the initial effluent stream 200 contains acetylene, methyl acetylene, propadiene, or other multiply unsaturated components, then the system of the present invention preferably includes a hydrogenation converter, e.g., an acetylene or MAPD converter, not shown. If incorporated into the present invention, the hydrogenation converter preferably receives and processes one or more of the following streams: the second overhead stream 211, the third bottoms stream 217, the fourth overhead stream 207 and/or the fourth bottoms stream 208. In the hydrogenation converter, acetylene contacts hydrogen and carbon dioxide under conditions effective to convert at least a portion of the acetylene to ethylene. Similarly, methyl acetylene and/or propadiene contact hydrogen and carbon dioxide under conditions effective to convert at least a portion of the methyl acetylene and/or propadiene to propylene. Components other than acetylene, methyl acetylene and propadiene that are present in the above-identified streams preferably pass unaltered through the hydrogenation converter(s). The resulting acetylene-depleted streams are then processed as described above with reference to FIG. 2.

Although the present invention is described herein with reference to FIGS. 1–3, these figures present only two of many possible embodiments of separation systems according to the present invention. The order of the various separation units described above, e.g., C2/C3 separator, C2 splitter, C3 splitter, light ends removal unit, and $C_4+$ component removal unit, may be varied without deviating in scope from the present invention.

The MTO Reaction Process

As discussed above, the present invention is particularly suited for use with an effluent derived from an MTO reaction system, which is discussed in more detail hereinafter.

Typically, molecular sieve catalysts have been used to convert oxygenate compounds to light olefins. Silicoaluminophosphate (SAPO) molecular sieve catalysts are particularly desirable in such a conversion process, because they are highly selective in the formation of ethylene and propylene. A non-limiting list of preferable SAPO molecular sieve catalysts includes SAPO-17, SAPO-18, SAPO-34, SAPO-35, SAPO-44, the substituted forms thereof, and mixtures thereof.

The feedstock preferably contains one or more aliphatic-containing compounds that include alcohols, amines, carbonyl compounds for example aldehydes, ketones and carboxylic acids, ethers, halides, mercaptans, sulfides, and the like, and mixtures thereof. The aliphatic moiety of the aliphatic-containing compounds typically contains from 1 to about 50 carbon atoms, preferably from 1 to 20 carbon atoms, more preferably from 1 to 10 carbon atoms, and most preferably from 1 to 4 carbon atoms.

Non-limiting examples of aliphatic-containing compounds include: alcohols such as methanol and ethanol, alkyl-mercaptans such as methyl mercaptan and ethyl mercaptan, alkyl-sulfides such as methyl sulfide, alkyl-amines such as methyl amine, alkyl-ethers such as DME, diethyl ether and methylethyl ether, alkyl-halides such as methyl chloride and ethyl chloride, alkyl ketones such as dimethyl ketone, alkyl-aldehydes such as formaldehyde and acetaldehyde, and various acids such as acetic acid.

In a preferred embodiment of the process of the invention, the feedstock contains one or more oxygenates, more specifically, one or more organic compound(s) containing at least one oxygen atom. In the most preferred embodiment of the process of invention, the oxygenate in the feedstock is one or more alcohol(s), preferably aliphatic alcohol(s) where the aliphatic moiety of the alcohol(s) has from 1 to 20 carbon atoms, preferably from 1 to 10 carbon atoms, and most preferably from 1 to 4 carbon atoms. The alcohols useful as feedstock in the process of the invention include lower straight and branched chain aliphatic alcohols and their unsaturated counterparts. Non-limiting examples of oxygenates include methanol, ethanol, n-propanol, isopropanol, methyl ethyl ether, DME, diethyl ether, di-isopropyl ether, formaldehyde, dimethyl carbonate, dimethyl ketone, acetic acid, and mixtures thereof. In the most preferred embodiment, the feedstock is selected from one or more of methanol, ethanol, DME, diethyl ether or a combination thereof, more preferably methanol and DME, and most preferably methanol.

The various feedstocks discussed above, particularly a feedstock containing an oxygenate, more particularly a feedstock containing an alcohol, is converted primarily into one or more olefin(s). The olefin(s) or olefin monomer(s) produced from the feedstock typically have from 2 to 30 carbon atoms, preferably 2 to 8 carbon atoms, more preferably 2 to 6 carbon atoms, still more preferably 2 to 4 carbons atoms, and most preferably ethylene an/or propylene.

Non-limiting examples of olefin monomer(s) include ethylene, propylene, butene-1, pentene-1, 4-methyl-pentene-1, hexene-1, octene-1 and decene-1, preferably ethylene, propylene, butene-1, pentene-1, 4-methyl-pentene-1, hexene-1, octene-1 and isomers thereof. Other olefin monomer(s) include unsaturated monomers, diolefins having 4 to 18 carbon atoms, conjugated or nonconjugated dienes, polyenes, vinyl monomers and cyclic olefins.

In the most preferred embodiment, the feedstock, preferably of one or more oxygenates, is converted in the presence of a molecular sieve catalyst composition into olefin(s) having 2 to 6 carbons atoms, preferably 2 to 4 carbon atoms. Most preferably, the olefin(s), alone or combination, are converted from a feedstock containing an oxygenate, preferably an alcohol, most preferably methanol, to the preferred olefin(s) ethylene and/or propylene.

The most preferred process is generally referred to as gas-to-olefins (GTO) or alternatively, methanol-to-olefins (MTO). In an MTO process, a methanol containing feedstock, is converted in the presence of a molecular sieve catalyst composition into one or more olefins, preferably and predominantly, ethylene and/or propylene, often referred to as light olefins.

The feedstock, in one embodiment, contains one or more diluents, typically used to reduce the concentration of the feedstock. The diluents are generally non-reactive to the feedstock or molecular sieve catalyst composition. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred. In other embodiments, the feedstock does not contain any diluent.

The diluent may be used either in a liquid or a vapor form, or a combination thereof. The diluent is either added directly to a feedstock entering into a reactor or added directly into a reactor, or added with a molecular sieve catalyst composition. In one embodiment, the amount of diluent in the feedstock is in the range of from about 1 to about 99 mole percent based on the total number of moles of the feedstock and diluent, preferably from about 1 to 80 mole percent, more preferably from about 5 to about 50, most preferably from about 5 to about 25. In one embodiment, other hydrocarbons are added to a feedstock either directly or indirectly, and include olefin(s), paraffin(s), aromatic(s) (see for example U.S. Pat. No. 4,677,242, addition of aromatics) or mixtures thereof, preferably propylene, butylene, pentylene, and other hydrocarbons having 4 or more carbon atoms, or mixtures thereof.

The process for converting a feedstock, especially a feedstock containing one or more oxygenates, in the presence of a molecular sieve catalyst composition of the invention, is carried out in a reaction process in a reactor, where the process is a fixed bed process, a fluidized bed process (includes a turbulent bed process), preferably a continuous fluidized bed process, and most preferably a continuous high velocity fluidized bed process.

The reaction processes can take place in a variety of catalytic reactors such as hybrid reactors that have a dense bed or fixed bed reaction zones and/or fast fluidized bed reaction zones coupled together, circulating fluidized bed reactors, riser reactors, and the like. Suitable conventional reactor types are described in for example U.S. Pat. Nos. 4,076,796, 6,287,522 (dual riser), and Fluidization Engineering, D. Kunii and O. Levenspiel, Robert E. Krieger Publishing Company, New York, N.Y. 1977, which are all herein fully incorporated by reference.

The preferred reactor type are riser reactors generally described in Riser Reactor, Fluidization and Fluid-Particle Systems, pages 48 to 59, F. A. Zenz and D. F. Othmer, Reinhold Publishing Corporation, New York, 1960, and U.S. Pat. No. 6,166,282 (fast-fluidized bed reactor), and U.S. patent application Ser. No. 09/564,613 filed May 4, 2000 (multiple riser reactor), which are all herein fully incorporated by reference.

In an embodiment, the amount of liquid feedstock fed separately or jointly with a vapor feedstock, to a reactor system is in the range of from 0.1 weight percent to about 85 weight percent, preferably from about 1 weight percent to about 75 weight percent, more preferably from about 5 weight percent to about 65 weight percent based on the total weight of the feedstock including any diluent contained therein. The liquid and vapor feedstocks are preferably the same composition, or contain varying proportions of the same or different feedstock with the same or different diluent.

The conversion temperature employed in the conversion process, specifically within the reactor system, is in the range of from about 392° F. (200° C.) to about 1832° F. (1000° C.), preferably from about 482° F. (250° C.) to about 1472° F. (800° C.), more preferably from about 482° F. (250° C.) to about 1382° F. (750° C.), yet more preferably from about 572° F. (300° C.) to about 1202° F. (650° C.), yet even more preferably from about 662° F. (350° C.) to about 1112° F. (600° C.) most preferably from about 662° F. (350° C.) to about 1022° F. (550° C.).

The conversion pressure employed in the conversion process, specifically within the reactor system, varies over a wide range including autogenous pressure. The conversion pressure is based on the partial pressure of the feedstock exclusive of any diluent therein. Typically the conversion pressure employed in the process is in the range of from about 0.1 kPaa to about 5 MPaa, preferably from about 5 kpaa to about 1 MPaa, and most preferably from about 20 kPaa to about 500 kPaa.

The weight hourly space velocity (WHSV), particularly in a process for converting a feedstock containing one or more oxygenates in the presence of a molecular sieve catalyst composition within a reaction zone, is defined as the total weight of the feedstock excluding any diluents to the reaction zone per hour per weight of molecular sieve in the molecular sieve catalyst composition in the reaction zone. The WHSV is maintained at a level sufficient to keep the catalyst composition in a fluidized state within a reactor.

Typically, the WHSV ranges from about 1 hr-1 to about 5000 hr-1, preferably from about 2 hr-1 to about 3000 hr-1, more preferably from about 5 hr-1 to about 1500 hr-1, and most preferably from about 10 hr-1 to about 1000 hr-1. In one preferred embodiment, the WHSV is greater than 20 hr-1, preferably the WHSV for conversion of a feedstock containing methanol, DME, or both, is in the range of from about 20 hr-1 to about 300 hr-1.

The superficial gas velocity (SGV) of the feedstock including diluent and reaction products within the reactor system is preferably sufficient to fluidize the molecular sieve catalyst composition within a reaction zone in the reactor. The SGV in the process, particularly within the reactor system, more particularly within the riser reactor(s), is at least about 0.1 meter per second (m/sec), preferably greater than 0.5 m/sec, more preferably greater than 1 m/sec, even more preferably greater than 2 m/sec, yet even more preferably greater than 3 m/sec, and most preferably greater than 4 m/sec. See for example U.S. patent application Ser. No. 09/708,753 filed Nov. 8, 2000, which is herein incorporated by reference.

Ethylene and Propylene Disposition

The ethylene and propylene streams treated and separated according to this invention can be polymerized to form plastic compositions, e.g., polyolefins, particularly polyethylene and polypropylene. Any conventional process for forming polyethylene or polypropylene can be used. Catalytic processes are preferred. Particularly preferred are metallocene, Ziegler/Natta, aluminum oxide and acid catalytic systems. See, for example, U.S. Pat. Nos. 3,258,455; 3,305, 538; 3,364,190; 5,892,079; 4,659,685; 4,076,698; 3,645, 992; 4,302,565; and 4,243,691, the catalyst and process descriptions of each being expressly incorporated herein by reference. In general, these methods involve contacting the ethylene or propylene product with a polyolefin-forming catalyst at a pressure and temperature effective to form the polyolefin product.

In one embodiment of this invention, the ethylene or propylene product is contacted with a metallocene catalyst to form a polyolefin. Desirably, the polyolefin forming process is carried out at a temperature ranging between about 50° C. and about 320° C. The reaction can be carried out at low, medium or high pressure, being anywhere within the range of about 1 bar to about 3200 bar. For processes carried out in solution, an inert diluent can be used. In this type of operation, it is desirable that the pressure be at a range of from about 10 bar to about 150 bar, and preferably at a temperature range of from about 120° C. to about 250° C. For gas phase processes, it is preferred that the temperature generally be within a range of about 60° C. to 120° C., and that the operating pressure be from about 5 bar to about 50 bar.

In addition to polyolefins, numerous other olefin derivatives can be formed from the ethylene, propylene and $C_{4+}$ olefins, particularly butylene, separated according to this invention. The olefins separated according to this invention can also be used in the manufacture of such compounds as aldehydes, acids such as C2–C13 mono carboxylic acids, alcohols such as C2–C12 mono alcohols, esters made from the C2–C12 mono carboxylic acids and the C2–C12 mono alcohols, linear alpha olefins, vinyl acetate, ethylene dicholoride and vinyl chloride, ethylbenzene, ethylene oxide, cumene, acrolein, allyl chloride, propylene oxide, acrylic acid, ethylene-propylene rubbers, and acrylonitrile, and trimers and dimers of ethylene and propylene. The $C_{4+}$ olefins, butylene in particular, are particularly suited for the manufacture of aldehydes, acids, alcohols, esters made from C5–C13 mono carboxylic acids and C5–C13 mono alcohols and linear alpha olefins.

Having now fully described the invention, it will be appreciated by those skilled in the art that the invention may be performed within a wide range of parameters within what is claimed, without departing from the spirit and scope of the invention.

We claim:

1. A process for removing dimethyl ether from an olefin-containing effluent stream, the process comprising the steps of:
   (a) providing the effluent stream, wherein the effluent stream comprises ethane, ethylene, propane, propylene and dimethyl ether;
   (b) contacting the effluent stream with an oxygenate removal medium in an oxygenate removal unit under conditions effective to form a first overhead stream and a first bottoms stream, wherein the first overhead stream comprises residual oxygenate removal medium and a majority of the ethane, ethylene, propane, propylene, and dimethyl ether, and wherein the first bottoms stream comprises a minority of the dimethyl ether and a majority of the oxygenate removal medium;
   (c) contacting the first overhead stream with water under conditions effective to form a second overhead stream and a second bottoms stream, wherein the second overhead stream comprises a majority of the ethane, ethylene, propane, propylene, and dimethyl ether present in the first overhead stream, and wherein the second bottoms stream comprises a majority of the residual oxygenate removal medium and a majority of the water; and
   (d) separating at least a portion of the second overhead stream into a third overhead stream and a third bottoms stream, wherein the third overhead stream comprises a majority of the propylene and optionally a majority of the ethane, ethylene and light ends present in the at least a portion of the second overhead stream, and wherein the third bottoms stream comprises a majority of the propane and dimethyl ether present in the at least a portion of the second overhead stream.

2. The process of claim 1, wherein the oxygenate-removal medium is selected from the group consisting of methanol and tri(ethylene glycol).

3. The process of claim 1, wherein the second overhead stream contains greater than 1000 wppm dimethyl ether, based on the total weight of the second overhead stream.

4. The process of claim 3, wherein the second overhead stream contains greater than 1500 wppm dimethyl ether, based on the total weight of the second overhead stream.

5. The process of claim 1, wherein the process further comprises the step of:
(e) separating chemical grade or purer propylene from at least a portion of the third overhead stream.

6. The process of claim 5, wherein the chemical grade or purer propylene is polymer grade propylene.

7. The process of claim 6, wherein the process further comprises the step of:
(f) polymerizing the polymer grade propylene.

8. The process of claim 1, wherein the process further comprises the step of:
(e) separating polymerization grade ethylene from at least a portion of the third overhead stream.

9. The process of claim 8, wherein the process further comprises the step of:
(f) polymerizing the polymerization grade ethylene.

10. The process of claim 1, wherein the olefin-containing effluent stream is derived from an oxygenate to olefin reaction system.

11. The process of claim 1, wherein the third bottoms stream comprises at least 1 weight percent dimethyl ether, based on the total weight of the third bottoms stream.

12. The process of claim 11, wherein the third bottoms stream comprises at least 10 weight percent dimethyl ether, based on the total weight of the third bottoms stream.

13. The process of claim 1, wherein the olefin-containing effluent stream, the first overhead stream and the second overhead stream further comprise $C_4+$ hydrocarbons, the process further comprising the step of:
(e) removing at least a majority of the $C_4$ hydrocarbons from the second overhead stream.

14. The process of claim 1, wherein the process further comprises the step of:
(e) removing at least a majority of the ethane from the second overhead stream.

15. The process of claim 1, wherein the process further comprises the step of:
(e) removing at least a majority of the light ends from the second overhead stream.

16. The process of claim 1, wherein the second overhead stream further comprises water, the process further comprising the step of:
(e) contacting at least a portion of the second overhead stream with a drying medium in a drying unit under conditions effective to remove at least a majority of the water from the at least a portion of the second overhead stream.

17. The process of claim 1, wherein the second overhead stream further comprises carbon dioxide, the process further comprising the step of:

(e) contacting at least a portion of the second overhead stream with a caustic medium under conditions effective to remove at least a majority of the carbon dioxide from the at least a portion of the second overhead stream.

18. A process for separating components from an olefin-containing effluent stream, the process comprising the steps of:
(a) providing the effluent stream, wherein the effluent stream comprises ethane, ethylene, propane, propylene and dimethyl ether;
(b) contacting the effluent stream with an oxygenate removal medium in an oxygenate removal unit under conditions effective to form a first overhead stream and a first bottoms stream, wherein the first overhead stream comprises residual oxygenate removal medium and a majority of the ethane, ethylene, propane, propylene, and dimethyl ether, and wherein the first bottoms stream comprises a minority of the dimethyl ether and a majority of the oxygenate removal medium;
(c) contacting the first overhead stream with water under conditions effective to form a second overhead stream and a second bottoms stream, wherein the second overhead stream comprises a majority of the ethane, ethylene, propane, propylene, and dimethyl ether present in the first overhead stream, and wherein the second bottoms stream comprises a majority of the residual oxygenate removal medium present in the first overhead stream and a majority of the water;
(d) separating at least a portion of the second overhead stream into a third overhead stream and a third bottoms stream, wherein the third overhead stream comprises a majority of the ethane and ethylene present in the at least a portion of the second overhead stream, and wherein the third bottoms stream comprises a majority of the propane, propylene and dimethyl ether present in the at least a portion of the second overhead stream; and
(e) separating at least a portion of the third bottoms stream into a fourth overhead stream and a fourth bottoms stream, wherein the fourth overhead stream comprises a majority of the propylene present in the at least a portion of the third bottoms stream, and wherein the fourth bottoms stream comprises a majority of the propane and dimethyl ether present in the at least a portion of the third bottoms stream.

19. The process of claim 18, wherein the oxygenate-removal medium is selected from the group consisting of methanol and tri(ethylene glycol).

20. The process of claim 18, wherein the second overhead stream contains greater than 1000 wppm dimethyl ether, based on the total weight of the second overhead stream.

21. The process of claim 20, wherein the second overhead stream contains greater than 1500 wppm dimethyl ether, based on the total weight of the second overhead stream.

22. The process of claim 18, wherein the process further comprises the step of:
(f) separating at least a portion of the third overhead stream into a fifth overhead stream and a fifth bottoms stream, wherein the fifth overhead stream contains a majority of the ethylene present in the at least a portion of the third overhead stream, and wherein the fifth bottoms stream contains a majority of the ethane present in the at least a portion of the third overhead stream.

23. The process of claim 22, wherein the process as further comprises the step of:

(g) polymerizing the ethylene from the fifth overhead stream.

24. The process of claim 18, wherein the process further comprises the step of:
    (f) combusting at least a portion of the fourth bottoms stream as fuel.

25. The process of claim 18, wherein the process further comprises the steps of:
    (f) feeding an oxygenate into a reactor; and
    (g) contacting the oxygenate with a molecular sieve catalyst composition in a reactor under conditions effective to convert at least a portion of the oxygenate to light olefins and optionally byproducts.

26. The process of claim 25, wherein step (g) occurs at an oxygenate conversion of from about 80 to about 99 weight percent, based on the total weight of oxygenate fed to the reactor in step (f).

27. The process of claim 26, wherein step (g) occurs at an oxygenate conversion of from about 93 to about 96 weight percent, based on the total weight of oxygenate fed to the reactor in step (f).

28. The process of claim 18, wherein the fourth bottoms stream comprises at least 1 weight percent dimethyl ether, based on the total weight of the fourth bottoms steam.

29. The process of claim 28, wherein the fourth bottoms stream comprises at least 10 weight percent dimethyl ether, based on the total weight of the fourth bottoms stream.

30. The process of claim 18, wherein the olefin-containing effluent stream, the first overhead stream, the second overhead stream, and the third overhead stream contain acetylene, the process further comprising the step of:
    (f) contacting the acetylene in at least a portion of the third overhead stream with hydrogen and carbon monoxide under conditions effective to convert at least a portion of the acetylene to ethylene.

31. The process of claim 18, wherein the olefin-containing effluent stream, the first overhead stream, the second overhead stream, and the third bottoms stream contain methyl acetylene or propadiene, the process further comprising the step of:
    (f) contacting the methyl acetylene or propadiene in at least a portion of the third bottoms stream with hydrogen and carbon monoxide under conditions effective to convert at least a portion of the methyl acetylene or propadiene to propylene.

32. The process of claim 18, wherein the effluent stream, the first overhead stream, the second overhead stream and the third overhead stream further contain methane, the process further comprising the step of:
    (f) separating at least a portion of the third overhead stream into a fifth overhead stream and a fifth bottoms stream, wherein the fifth overhead stream contains a majority of the methane present in the at least a portion of the third overhead stream, and wherein the fifth bottoms stream contains a majority of the ethylene and ethane present in the at least a portion of the second overhead stream.

33. The process of claim 32, wherein the process further comprises the step of:
    (g) separating at least a portion of the fifth bottoms into a sixth overhead stream and a sixth bottoms stream, wherein the sixth overhead stream contains a majority of the ethylene present in the at least a portion of the fifth bottoms stream, and wherein the sixth bottoms stream contains a majority of the ethane present in the at least a portion of the fifth bottoms stream.

34. The process of claim 32, wherein the olefin-containing effluent stream, the first overhead stream, the second overhead stream, the third overhead stream, and the fifth bottoms stream contain acetylene, the process further comprising the step of:
    (g) contacting the acetylene in at least a portion of the fifth bottoms stream with hydrogen and carbon monoxide under conditions effective to convert at least a portion of the acetylene to ethylene.

35. The process of claim 18, wherein the olefin-containing effluent stream contains from 50 to 95 combined weight percent ethylene and propylene, based on the total weight of the olefin-containing effluent stream.

36. The process of claim 18, wherein the olefin-containing effluent stream contains from 25 to 75 weight percent ethylene, based on the total weight of the olefin-containing effluent stream.

37. The process of claim 18, wherein the olefin-containing effluent stream contains from 25 to 75 weight percent propylene, based on the total weight of the olefin-containing effluent steam.

38. The process of claim 18, wherein the olefin-containing effluent stream, the first overhead stream and the second overhead stream further contain carbon dioxide, the process further comprising the step of:
    (f) contacting the second overhead stream with a caustic medium under conditions effective to remove at least a majority of the carbon dioxide from the second overhead stream.

39. The process of claim 38, wherein the olefin-containing effluent stream, the first overhead stream and the second overhead stream further contain $C_4+$ hydrocarbons, the process further comprising the step of:
    (g) separating at least a majority of the $C_4+$ hydrocarbons from the second overhead stream.

40. The process of claim 18, wherein the second overhead stream further contains water, the process further comprising the step of:
    (f) contacting the second overhead stream with a drying medium in a drying unit under conditions effective to remove at least a majority of the water from the second overhead stream.

41. The process of claim 18, wherein the olefin-containing effluent stream, the first overhead stream and the second overhead stream further contain $C_4+$ hydrocarbons, the process further comprising the step of:
    (f) separating at least a majority of the $C_4+$ hydrocarbons from the second overhead stream.

42. The process of claim 18, wherein the process further comprises the step of:
    (f) polymerizing the propylene from the fourth overhead stream.

43. A process for separating components from an olefin-containing effluent steam, the process comprising the steps of:
    (a) providing the olefin-containing effluent stream, wherein the effluent stream contains ethane, ethylene, propane, propylene, dimethyl ether and one or more oxygenates, wherein the one or more oxygenates are selected from the group consisting of methyl ethyl ether, ethanol, isopropanol, acetic acid, propionic acid, ethanal, butanal, propanal, acetone, 2-butanone, 2-pentanone, 4-methyl-2-pentanone and methyl acetate;
    (b) contacting the effluent stream with an oxygenate removal medium in an oxygenate removal unit under conditions effective to form a first overhead stream and a first bottoms steam, wherein the first overhead stream contains a majority of the ethane, ethylene, propane, propylene, and dimethyl ether present in the effluent stream and residual oxygenate removal medium, and wherein the first bottoms stream contains a majority of the oxygenate removal medium, a majority of the oxygenates present in the effluent stream, and a minority of the dimethyl ether present in the effluent stream;

(c) contacting the first overhead stream with water under conditions effective to form a second overhead stream and a second bottoms stream, wherein the second overhead stream contains a majority of the ethane, ethylene, propane, propylene, and dimethyl ether present in the first overhead stream, and wherein the second bottoms stream contains a majority of the residual oxygenate medium present in the first overhead stream and a majority of the water;

(d) separating at least a portion of the second overhead stream into a third overhead stream and a third bottoms stream, wherein the third overhead stream contains a majority of the ethane and ethylene present in the at least a portion of the second overhead stream, and wherein the third bottoms stream contains a majority of the propane, propylene and dimethyl ether present in the at least a portion of the second overhead stream; and (e) separating at least a portion of the third bottoms stream into a fourth overhead steam and a fourth bottoms stream, wherein the fourth overhead stream contains a majority of the propylene present in the at least a portion of the third bottoms stream, and wherein the fourth bottoms stream contains a majority of the propane and dimethyl ether present in the at least a portion of the third bottoms stream.

44. The process of claim 43, wherein the oxygenate-removal medium is selected from the group consisting of methanol and tri(ethylene glycol).

45. The process of claim 43, wherein the second overhead stream contains greater than 1000 wppm dimethyl ether, based on the total weight of the second overhead stream.

46. The process of claim 45, wherein the second overhead stream contains greater than 1500 wppm dimethyl ether, based on the total weight of the second overhead stream.

47. The process of claim 43, wherein the process further comprises the step of:

(f) separating at least a portion of the third overhead stream into a fifth overhead stream and a fifth bottoms stream, wherein the fifth overhead stream contains a majority of the ethylene present in the at least a portion of the third overhead stream, and wherein the fifth bottoms stream contains a majority of the ethane present in the at least a portion of the third overhead stream.

48. The process of claim 47, wherein the process further comprises the step of:

(g) polymerizing the ethylene from the fifth overhead stream.

49. The process of claim 43, wherein the process further comprises the step of:

(f) combusting at least a portion of the fourth bottoms stream as fuel.

50. The process of claim 43, wherein the process further comprises the steps of:

(f) feeding methanol into a reactor; and (g) contacting the methanol with a molecular sieve catalyst composition in a reactor under conditions effective to convert a portion of the methanol to light olefins and, optionally byproducts.

51. The process of claim 50, wherein step (g) occurs at a methanol conversion of from about 80 to about 99 weight percent, based on the total weight of the methanol fed to the reactor in step (f).

52. The process of claim 51, wherein step (g) occurs at a methanol conversion of from about 93 to about 96 weight percent, based on the total weight of the methanol fed to the reactor in step (f).

53. The process of claim 43, wherein the fourth bottoms stream comprises at least 1 weight percent dimethyl ether, based on the total weight of the fourth bottoms stream.

54. The process of claim 53, wherein the fourth bottoms stream comprises at least 10 weight percent dimethyl ether, based on the total weight of the fourth bottoms stream.

55. The process of claim 43, wherein the olefin-containing effluent stream, the first overhead stream, the second overhead stream, and the third overhead stream contain acetylene, the process further comprising the step of:

(f) contacting the acetylene in at least a portion of the third overhead stream with hydrogen and carbon monoxide under conditions effective to convert at least a portion of the acetylene to ethylene.

56. The process of claim 43, wherein the olefin-containing effluent stream, the first overhead stream, the second overhead stream, and the third bottoms stream contain methyl acetylene or propadiene, the process further comprising the step of:

(f) contacting the methyl acetylene or propadiene in at least a portion of the third bottoms stream with hydrogen and carbon monoxide under conditions effective to convert at least a portion of the methyl acetylene or propadiene to propylene.

57. The process of claim 43, wherein the effluent stream, the first overhead stream, the second overhead stream and the third overhead stream further contain methane, the process further comprising the step of:

(f) separating at least a portion of the third overhead stream into a fifth overhead stream and a fifth bottoms stream, wherein the fifth overhead stream contains a majority of the methane present in the at least a portion of the third overhead stream, and wherein the fifth bottoms stream contains a majority of the ethylene and ethane present in the at least a portion of the second overhead stream.

58. The process of claim 57, wherein the process further comprises the step of:

(g) separating at least a portion of the fifth bottoms stream into a sixth overhead stream and a sixth bottoms stream, wherein the sixth overhead stream contains a majority of the ethylene present in the at least a portion of the fifth bottoms stream, and wherein the sixth bottoms stream contains a majority of the ethane present in the at least a portion of the fifth bottoms stream.

59. The process of claim 57, wherein the olefin-containing effluent stream, the first overhead stream, the second overhead stream, the third overhead stream, and the fifth bottoms stream contain acetylene, the process further comprising the step of:

(g) contacting the acetylene in at least a portion of the fifth bottoms stream with hydrogen and carbon monoxide under conditions effective to convert at least a portion of the acetylene to ethylene.

60. The process of claim 43, wherein the olefin-containing effluent stream contains from 50 to 95 combined weight percent ethylene and propylene, based on the total weight of the olefin-containing effluent stream.

61. The process of claim 43, wherein the olefin-containing effluent stream contains from 25 to 75 weight percent ethylene, based on the total weight of the olefin-containing effluent stream.

62. The process of claim 43, wherein the olefin-containing effluent stream contains from 25 to 75 weight percent propylene, based on the total weight of the olefin-containing effluent stream.

63. The process of claim 43, wherein the olefin-containing effluent stream, the first overhead stream and the second overhead stream further contain carbon dioxide, the process further comprising the step of:
(f) contacting the second overhead stream with caustic medium under conditions effective to remove at least a majority of the carbon dioxide from the second overhead stream.

64. The process of claim 63, wherein the olefin-containing effluent stream, the first overhead stream and the second overhead stream further contain $C_4+$ hydrocarbons, the process further comprising the step of:
(g) separating at least a majority of the $C_4+$ hydrocarbons from the second overhead stream.

65. The process of claim 43, wherein the second overhead stream further contains water, the process further comprising the step of:
(f) contacting the second overhead stream with a drying medium in a drying unit under conditions effective to remove at least a majority of the water from the second overhead stream.

66. The process of claim 43, wherein the olefin-containing effluent stream, the first overhead stream and the second overhead stream further contain $C_4+$ hydrocarbons, the process further comprising the step of:
(f) separating at least a majority of the $C_4+$ hydrocarbons from the second overhead stream.

67. The process of claim 43, wherein the process further comprises the step of:
(f) polymerizing the propylene from the fourth overhead stream.

68. A process for separating components from an olefin-containing effluent stream, the process comprising the steps of:
(a) contacting an oxygenate with a molecular sieve catalyst composition in a reactor under conditions effective to form the effluent stream, wherein the effluent stream contains water, ethane, ethylene, propane, propylene, dimethyl ether and one or more oxygenate byproducts, wherein the oxygenate byproducts are selected from the group consisting of methyl ethyl ether, ethanol, isopropanol, acetic acid, propionic acid, ethanal, butanal, propanal, acetone, 2-butanone, 2-pentanone, 4-methyl-2-pentanone and methyl acetate;
(b) cooling at least a portion of the effluent under conditions effective to form a quench overhead stream and a condensed stream, wherein the quench overhead stream comprises a majority of the ethane, ethylene, propane, propylene, dimethyl ether and the one or more oxygenate byproducts present in the effluent stream, and wherein the condensed stream contains a majority of the water present in the effluent stream;
(c) contacting the quench overhead stream with an oxygenate removal medium in an oxygenate removal unit under conditions effective to form a first overhead stream and a first bottoms stream, wherein the first overhead stream contains a majority of the ethane, ethylene, propane, propylene, and dimethyl ether present in the quench overhead stream and residual oxygenate removal medium, and wherein the first bottoms stream contains a majority of the oxygenate removal medium, a majority of the oxygenate byproducts present in the quench overhead stream, and a minority of the dimethyl ether present in the quench overhead stream;
(d) contacting the first overhead stream with water under conditions effective to form a second overhead stream and a second bottoms stream, wherein the second overhead stream contains a majority of the ethane, ethylene, propane, propylene, and dimethyl ether present in the first overhead stream, and wherein the second bottoms stream contains a majority of the residual oxygenate removal medium present in the first overhead stream and a majority of the water contacted with the first overhead stream in step (d);
(e) separating at least a portion of the second overhead stream into a third overhead stream and a third bottoms stream, wherein the third overhead stream contains a majority of the ethane and ethylene present in the at least a portion of the second overhead stream, and wherein the third bottoms stream contains a majority of the propane, propylene and dimethyl ether present in the at least a portion of the second overhead stream; and
(f) separating at least a portion of the third bottoms stream into a fourth overhead stream and a fourth bottoms stream, wherein the fourth overhead stream contains a majority of the propylene present in the at least a portion of the third bottoms stream, and wherein the fourth bottoms stream contains a majority of the propane and dimethyl ether present in the at least a portion of the third bottoms stream.

69. The process of claim 68, wherein the oxygenate-removal medium is selected from the group consisting of methanol and tri(ethylene glycol).

70. The process of claim 68, wherein the second overhead stream contains greater than 1000 wppm dimethyl ether, based on the total weight of the second overhead stream.

71. The process of claim 70, wherein the second overhead stream contains greater than 1500 wppm dimethyl ether, based on the total weight of the second overhead stream.

72. The process of claim 68, wherein the process further comprises the step of:
(g) separating at least a portion of the third overhead stream into a fifth overhead stream and a fifth bottoms stream, wherein the fifth overhead stream contains a majority of the ethylene present in the at least a portion of the third overhead stream, and wherein the fifth bottoms stream contains a majority of the ethane present in the at least a portion of the third overhead stream.

73. The process of claim 72, wherein the process further comprises the step of:
(h) polymerizing the ethylene from the fifth overhead stream.

74. The process of claim 68, wherein the process further comprises the step of:
(g) combusting at least a portion of the fourth bottoms stream as fuel.

75. The process of claim 68, wherein step (a) occurs at an oxygenate conversion of from about 80 to about 99 weight percent, based on the total weight of the oxygenate introduced into the reactor.

76. The process of claim 75, wherein step (a) occurs at an oxygenate conversion of from about 93 to about 96 weight percent, based on the total weight of the oxygenate introduced into the reactor.

77. The process of claim 68, wherein the fourth bottoms stream comprises at least 1 weight percent dimethyl ether, based on the total weight of the fourth bottoms stream.

78. The process of claim 77, wherein the fourth bottoms stream comprises at least 10 weight percent dimethyl ether, based on the total weight of the fourth bottoms stream.

79. The process of claim 68, wherein the olefin-containing effluent stream, the quench overhead stream, the first overhead stream, the second overhead stream, and the third overhead stream contain acetylene, the process further comprising the step of:
(g) contacting the acetylene in at least a portion of the third overhead stream with hydrogen and carbon monoxide under conditions effective to convert at least a portion of the acetylene to ethylene.

80. The process of claim 68, wherein the olefin-containing effluent stream, the quench overhead stream, the first overhead stream, the second overhead stream, and the third bottoms stream contain methyl acetylene or propadiene, the process further comprising the step of:
(g) contacting the methyl acetylene or propadiene in at least a portion of the third bottoms stream with hydrogen and carbon monoxide under conditions effective to convert at least a portion of the methyl acetylene or propadiene to propylene.

81. The process of claim 68, wherein the effluent stream, the quench overhead stream, the first overhead stream, the second overhead stream and the third overhead stream further contain methane, the process further comprising the step of:
(g) separating at least a portion of the third overhead stream into a fifth overhead stream and a fifth bottoms stream, wherein the fifth overhead stream contains a majority of the methane present in the at least a portion of the third overhead stream, and wherein the fifth bottoms stream contains a majority of the ethylene and ethane present in the at least a portion of the second overhead stream.

82. The process of claim 81, wherein the process further comprises the step of:
(h) separating at least a portion of the fifth bottoms stream into a sixth overhead stream and a sixth bottoms stream, wherein the sixth overhead stream contains a majority of the ethylene present in the at least a portion of the fifth bottoms stream, and wherein the sixth bottoms stream contains a majority of the ethane present in the at least a portion of the fifth bottoms stream.

83. The process of claim 81, wherein the olefin-containing effluent stream, the quench overhead stream, the first overhead stream, the second overhead stream, the third overhead stream, and the fifth bottoms stream contain acetylene, the process further comprising the step of:
(h) contacting the acetylene in at least a portion of the fifth bottoms stream with hydrogen and carbon monoxide under conditions effective to convert at least a portion of the acetylene to ethylene.

84. The process of claim 68, wherein the olefin-containing effluent stream contains from 50 to 95 combined weight percent ethylene and propylene, based on the total weight of the olefin-containing effluent stream.

85. The process of claim 84, wherein the olefin-containing effluent stream contains from 25 to 75 weight percent ethylene, based on the total weight of the olefin-containing effluent stream.

86. The process of claim 68, wherein the olefin-containing effluent stream contains from 25 to 75 weight percent propylene, based on the total weight of the olefin-containing effluent stream.

87. The process of claim 68, wherein the olefin-containing effluent stream, the quench overhead stream, the first overhead stream and the second overhead stream further contain carbon dioxide, the process further comprising the step of:
(g) contacting the second overhead stream with a caustic medium under conditions effective to remove at least a majority of the carbon dioxide from the second overhead stream.

88. The process of claim 87, wherein the olefin-containing effluent stream, the quench overhead stream, the first overhead stream and the second overhead stream further contain $C_4+$ hydrocarbons, the process further comprising the step of:
(h) separating at least a majority of the $C_4+$ hydrocarbons from the second overhead stream.

89. The process of claim 68, wherein the second overhead stream further contains water, the process further comprising the step of:
(g) contacting the second overhead stream with a drying medium in a drying unit under conditions effective to remove at least a majority of the water from the second overhead stream.

90. The process of claim 68, wherein the olefin-containing effluent stream, the quench overhead stream, the first overhead stream and the second overhead stream further contain $C_4+$ hydrocarbons, the process further comprising the step of:
(g) separating at least a majority of the $C_4+$ hydrocarbons from the second overhead stream.

91. The process of claim 68, wherein the process further comprises the step of:
(g) polymerizing the propylene from the fourth overhead stream.

* * * * *